US010842393B2

(12) United States Patent
Watanabe

(10) Patent No.: US 10,842,393 B2
(45) Date of Patent: Nov. 24, 2020

(54) BIOLOGICAL INFORMATION DETECTION APPARATUS THAT INCLUDES A LIGHT SOURCE PROJECTING A NEAR-INFRARED PATTERN ONTO AN OBJECT AND AN IMAGING SYSTEM INCLUDING FIRST PHOTODETECTOR CELLS DETECTING NEAR-INFRARED WAVELENGTH LIGHT AND SECOND PHOTODETECTOR CELLS DETECTING VISIBLE WAVELENGTH LIGHT

(71) Applicant: Panasonic Intellectual Property Management Co., Ltd., Osaka (JP)

(72) Inventor: Hisashi Watanabe, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 354 days.

(21) Appl. No.: 15/813,223

(22) Filed: Nov. 15, 2017

(65) Prior Publication Data
US 2018/0153422 A1 Jun. 7, 2018

(30) Foreign Application Priority Data
Dec. 1, 2016 (JP) .................. 2016-234116

(51) Int. Cl.
*A61B 5/024* (2006.01)
*A61B 5/026* (2006.01)
(Continued)

(52) U.S. Cl.
CPC ........ *A61B 5/02433* (2013.01); *A61B 5/0059* (2013.01); *A61B 5/0261* (2013.01); *A61B 6/563* (2013.01); *G06T 2207/10048* (2013.01)

(58) Field of Classification Search
CPC ... A61B 5/02433; A61B 6/563; A61B 5/0059; A61B 5/0261; A61B 5/14551; A61B 5/024; A61B 5/0205; G06T 2207/10048
See application file for complete search history.

(56) References Cited

U.S. PATENT DOCUMENTS 6,859,658 B1  2/2005  Krug
7,648,463 B1*  1/2010  Elhag .................. A61B 5/6814
                                              600/504
(Continued)

FOREIGN PATENT DOCUMENTS

JP       6-054836    3/1994
JP    2002-200050    7/2002
(Continued)

OTHER PUBLICATIONS

Tsutomu Kuroda et al., "Analysis of facial color and skin temperature in emotional change and its synthesis of facial color", Human Interface Society, vol. 1, No. 1, Feb. 16, 1999, pp. 15-20 (Whole sentence Translation).

Primary Examiner — Mohammad K Islam
(74) Attorney, Agent, or Firm — McDermott Will & Emery LLP

(57) ABSTRACT

A biological information detection apparatus includes: a light source which projects a pattern of near-infrared light onto an object including a living body; an imaging system which includes first photodetector cells detecting light in a near-infrared wavelength range and second photodetector cells detecting light in a visible wavelength range, and generates a first image signal representing a first image, which is an image taken in the near-infrared wavelength range, of the object on which the pattern is projected, and a second image signal representing a second image of the object taken in the visible wavelength range; and a calculator which calculates biological information concerning the (Continued)

living body using at least one selected from the group consisting of the first and second image signals.

17 Claims, 21 Drawing Sheets

(51) Int. Cl.
*A61B 6/00* (2006.01)
*A61B 5/00* (2006.01)

(56) References Cited

U.S. PATENT DOCUMENTS

| | | | | |
|---|---|---|---|---|
| 8,503,712 B2* | 8/2013 | Ahmed | ............... | G06T 7/0014 |
| | | | | 382/100 |
| 8,730,321 B2* | 5/2014 | Luciano | ............... | A61B 5/0059 |
| | | | | 348/135 |
| 9,968,285 B2* | 5/2018 | Valsan | ............... | A61B 5/489 |
| 10,121,073 B2* | 11/2018 | Smits | ............... | G06K 9/00604 |
| 10,366,475 B2* | 7/2019 | Naruse | ............... | H04N 9/045 |
| 10,699,395 B2* | 6/2020 | Kurihara | ............... | G06T 5/002 |
| 2003/0069485 A1* | 4/2003 | Konishi | ............... | A61B 5/1455 |
| | | | | 600/317 |
| 2006/0184040 A1* | 8/2006 | Keller | ............... | A61B 5/445 |
| | | | | 600/476 |
| 2008/0027317 A1* | 1/2008 | Wood | ............... | A61B 5/0059 |
| | | | | 600/427 |
| 2009/0028461 A1* | 1/2009 | Wieringa | ............. | A61B 5/0059 |
| | | | | 382/284 |
| 2011/0235017 A1* | 9/2011 | Iwasaki | ............... | H04N 5/332 |
| | | | | 356/4.01 |
| 2012/0265039 A1* | 10/2012 | Kiani | ............... | A61B 5/7271 |
| | | | | 600/323 |
| 2013/0229711 A1* | 9/2013 | Kato | ............... | G02B 30/00 |
| | | | | 359/464 |
| 2013/0329031 A1* | 12/2013 | Miura | ............... | G06K 9/2018 |
| | | | | 348/77 |
| 2014/0187879 A1* | 7/2014 | Wood | ............... | A61B 18/20 |
| | | | | 600/317 |
| 2014/0303454 A1 | 10/2014 | Clifton et al. | | |
| 2016/0022181 A1* | 1/2016 | Valsan | ............... | A61B 5/489 |
| | | | | 600/324 |
| 2016/0262626 A1* | 9/2016 | Pelosi | ............... | A61B 5/0077 |
| 2017/0231490 A1* | 8/2017 | Toth | ............... | A61B 3/113 |
| | | | | 600/558 |
| 2019/0073523 A1* | 3/2019 | Lee | ............... | A61B 5/1107 |

FOREIGN PATENT DOCUMENTS

| | | |
|---|---|---|
| JP | 2003-517342 | 5/2003 |
| JP | 2005-218507 | 8/2005 |
| JP | 2008-237244 | 10/2008 |
| JP | 2014-000246 | 1/2014 |
| JP | 2014-527863 | 10/2014 |
| WO | 2000/027276 | 5/2000 |
| WO | 2015/121070 | 8/2015 |

* cited by examiner

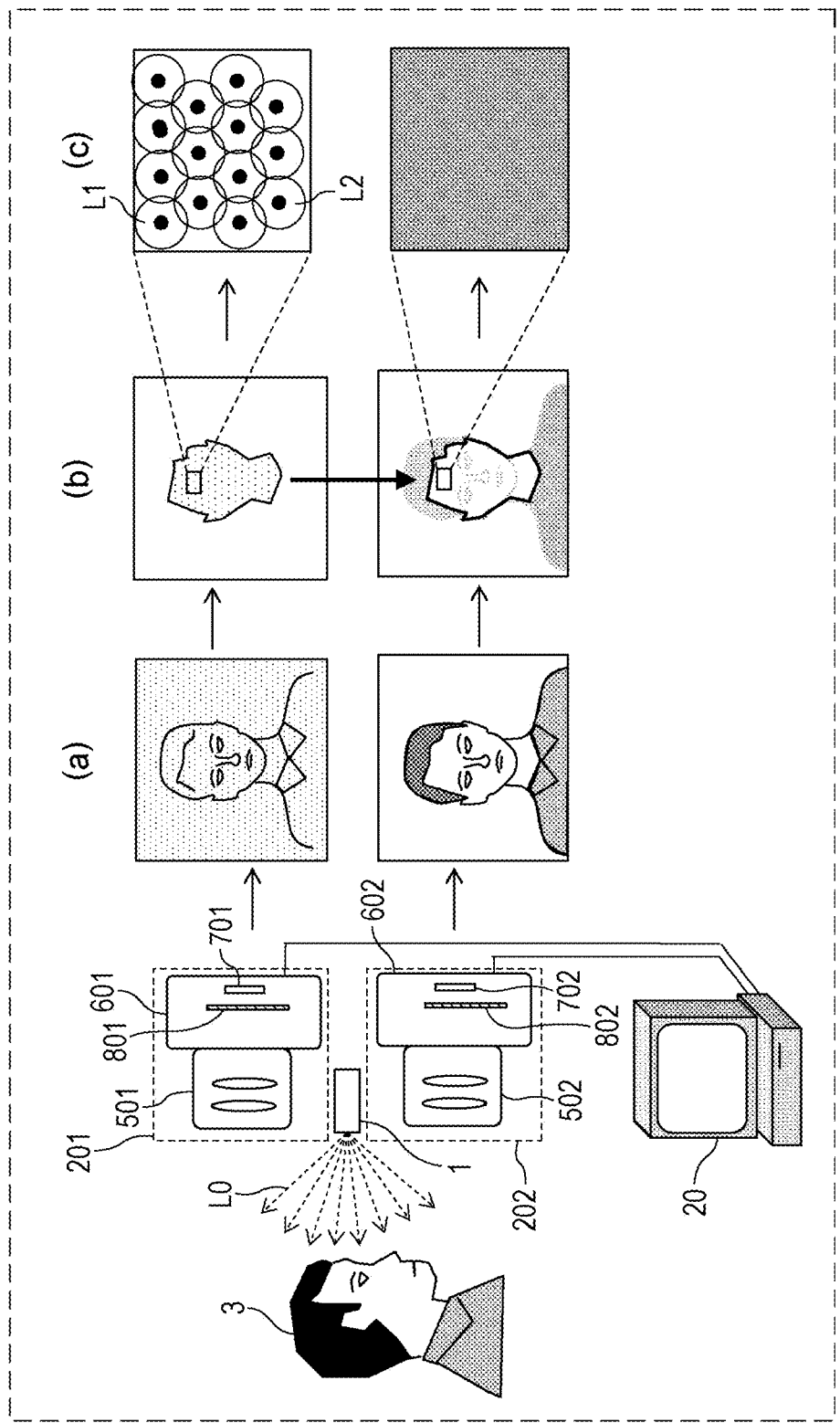

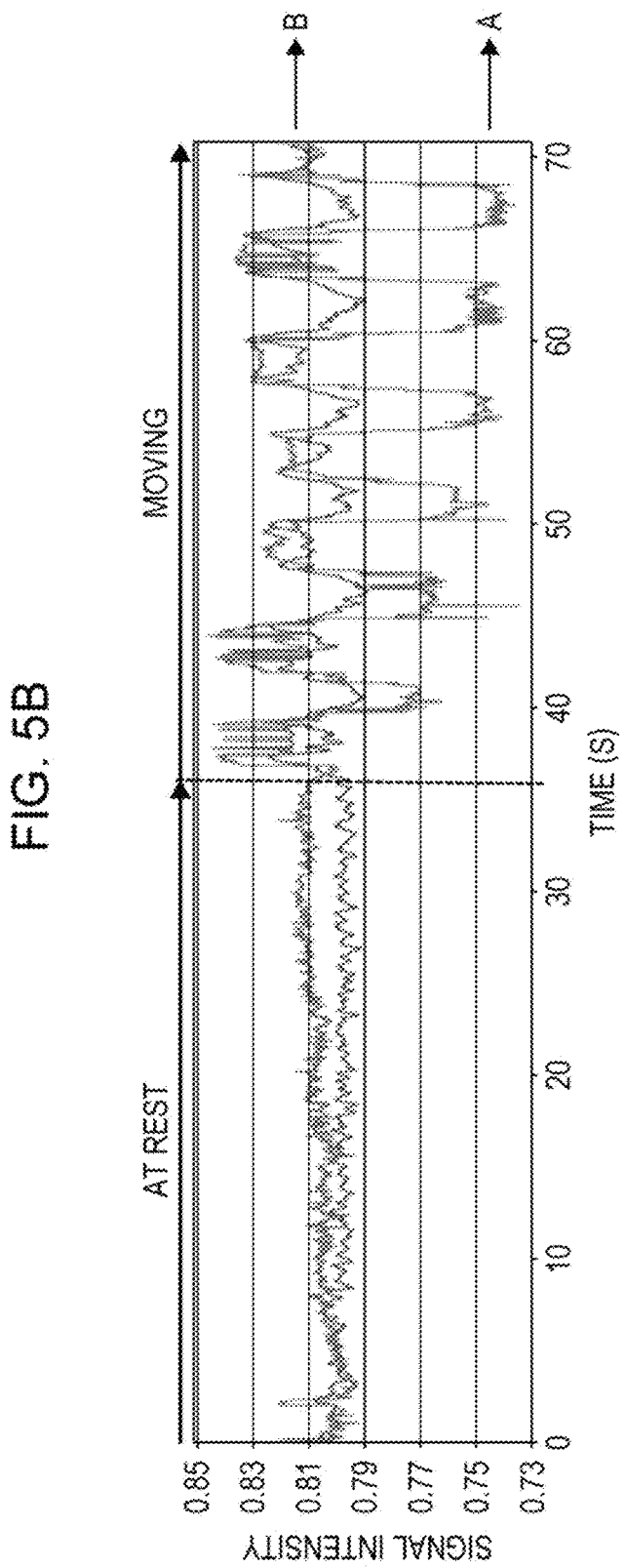

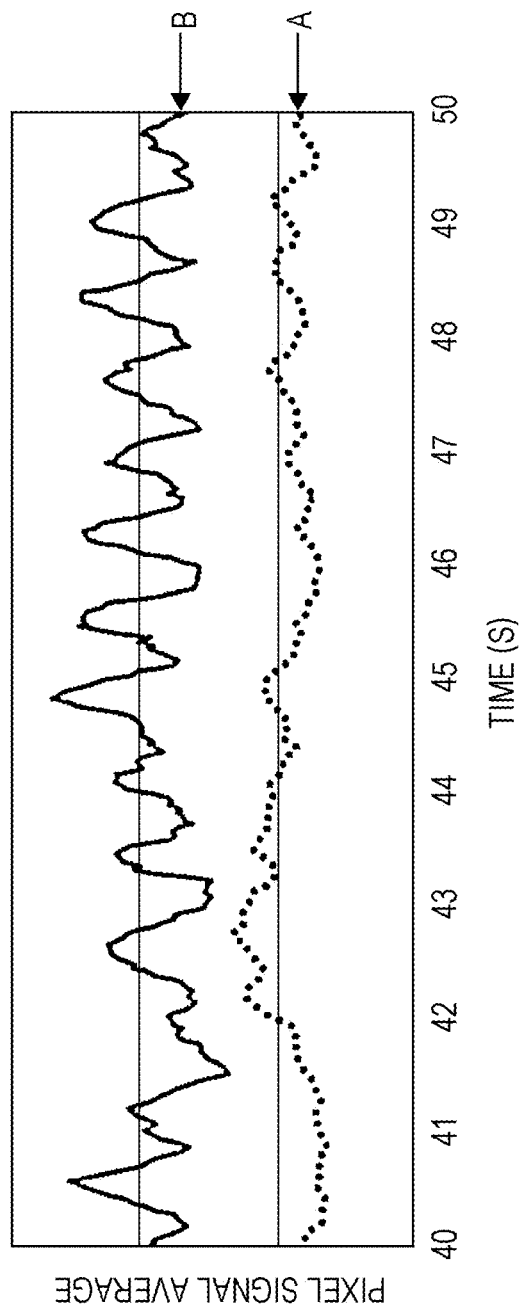

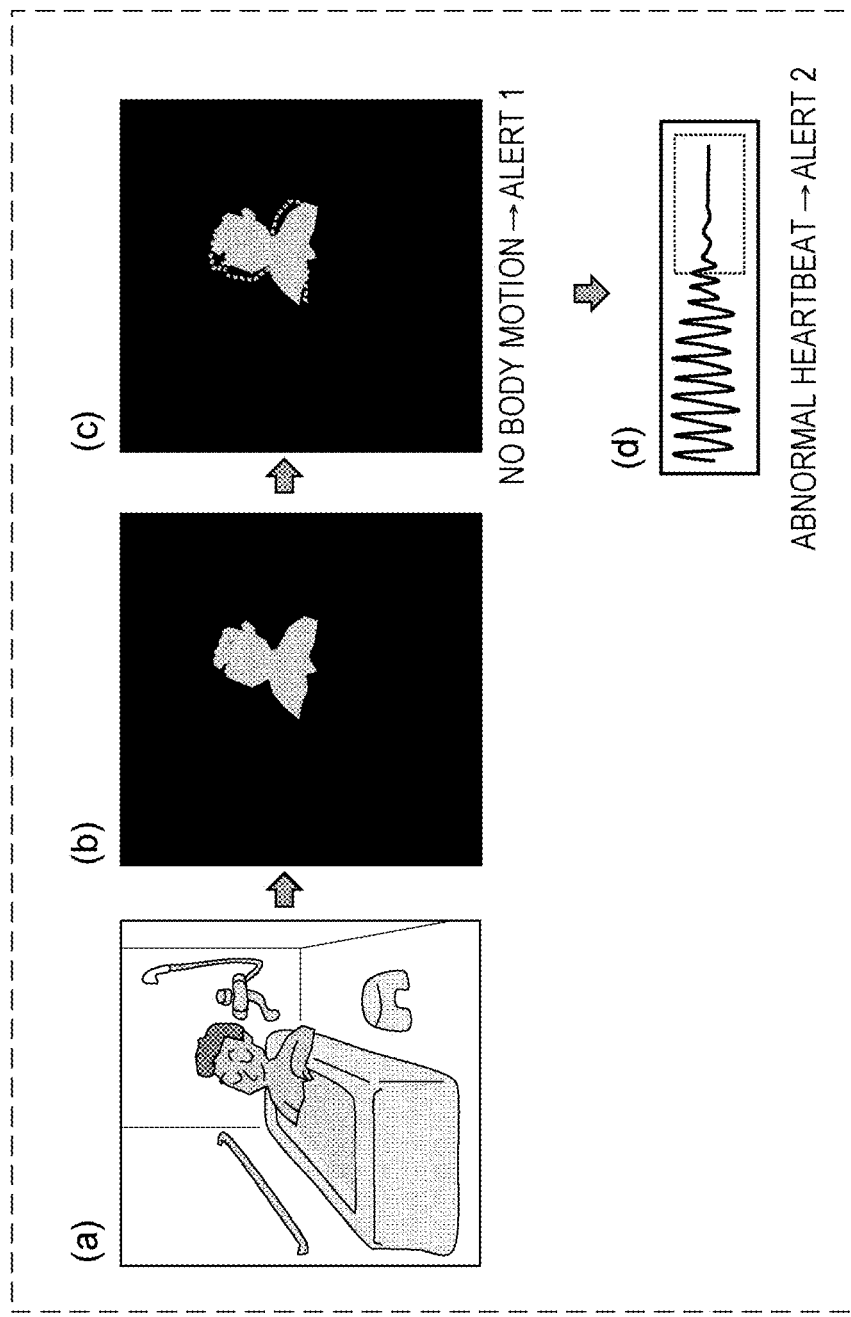

BIOLOGICAL INFORMATION DETECTION APPARATUS THAT INCLUDES A LIGHT SOURCE PROJECTING A NEAR-INFRARED PATTERN ONTO AN OBJECT AND AN IMAGING SYSTEM INCLUDING FIRST PHOTODETECTOR CELLS DETECTING NEAR-INFRARED WAVELENGTH LIGHT AND SECOND PHOTODETECTOR CELLS DETECTING VISIBLE WAVELENGTH LIGHT

BACKGROUND

1. Technical Field

The present disclosure relates to a biological information detection apparatus. The present disclosure relates to a biological information detection apparatus which detects biological information, such as heartbeat, in a non-contact manner, for example.

2. Description of the Related Art

As basic parameters to determine the health condition of human beings, heartbeat, blood flow, blood pressure, blood oxygen saturation, and the like are widely used. These kinds of biological information concerning blood are usually measured by contact-type measuring instruments. Such a contact-type measuring instrument is attached to the living body of a subject, giving the subject a feeling of discomfort particularly in long-period continuing measurement.

There have been various attempts to easily measure basic biological information to determine the health condition of human beings. For example, Japanese Unexamined Patent Application Publication No. 2005-218507 discloses a method of detecting heart rate from image information of a face or the like captured by a camera in a non-contact manner. Japanese Unexamined Patent Application Publication (Translation of PCT Application) No. 2003-517342 discloses a method of measuring blood oxygen saturation using a white light source and a laser source, based on the laser Doppler effect of laser light scattered behind the surface of the living body. Japanese Unexamined Patent Application Publication (Translation of PCT Application) No. 2014-527863 discloses a method of measuring the blood oxygen saturation by using a normal color camera while eliminating the influence of the ambient light.

On the other hand, a lot of methods to estimate psychological changes of human have been proposed. For example, Japanese Unexamined Patent Application Publication Nos. 6-54836 and 2008-237244 disclose methods of detecting a decrease in temperature of part around the nose by using thermography. The temperature of part around the nose decreases when human beings feel stressed (nervous) or are concentrated.

SUMMARY

In one general aspect, the techniques disclosed here feature a biological information detection apparatus, including: a light source which projects a pattern of near-infrared light onto an object including a living body; an imaging system which includes first photodetector cells detecting light in a near-infrared wavelength range and second photodetector cells detecting light in a visible wavelength range, generates a first image signal representing a first image, and a second image signal representing a second image; and a calculator which calculates biological information concerning the living body using at least one selected from the group consisting of the first and second image signals. The first image is an image of the object on which the pattern is projected, the image taken in the near-infrared wavelength range. The second image is an image of the object taken in the visible wavelength range.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 4A is a diagram schematically illustrating the configuration of a biological information detection apparatus and outputted image data in a first embodiment;

FIG. 5B is an explanatory diagram illustrating the effect of body motion compensation of Embodiment 1;

FIG. 5C is an explanatory diagram illustrating signal processing for biological information acquisition in Embodiment 1;

FIG. 13A is an explanatory view of a monitoring system using the biological information detection apparatus of Embodiment 4;

Figure 1A:
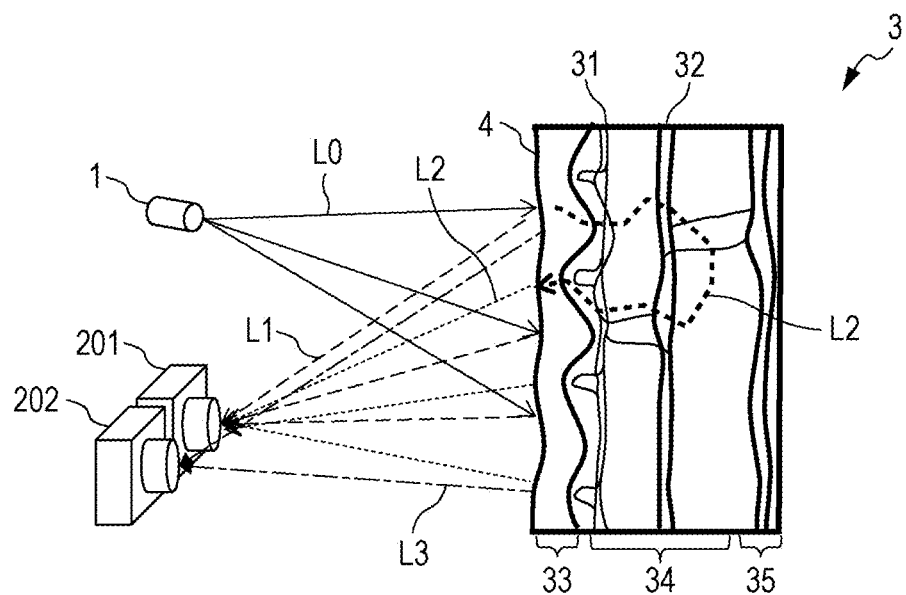
FIG. 1A is a schematic diagram illustrating the configuration of a biological information detection apparatus in an embodiment of the present disclosure.

DETAILED DESCRIPTION (Underlying Knowledge Forming Basis of the Present Disclosure)

Before description of embodiments of the present disclosure, the underlying knowledge forming basis of the present disclosure is described.

As described above, there have been various attempts to measure basic biological information to determine the health condition of human beings. For example, Japanese Unexamined Patent Application Publication No. 2005-218507 proposes a method of detecting the heart rate in a non-contact manner from image information of a face or the like captured by a camera. In the method of Japanese Unexamined Patent Application Publication No. 2005-218507, the heart rate is calculated by analyzing spatial frequency components of an acquired color image. In this method, the accuracy is reduced due to ambient light, such as room illumination, and it is difficult to stably detect the heart rate.

Blood oxygen saturation is measured generally using a pulse oximeter. A pulse oximeter sandwiches a finger and irradiates the finger with light having two wavelengths included in the red to near-infrared wavelength range, for measuring the transmittance thereof. The pulse oximeter thereby calculates the ratio in concentration of oxyhemoglobin to that of deoxyhemoglobin in blood. The pulse oximeter is able to measure blood oxygen saturation with a simple configuration. However, the pulse oximeter is a contact-type device and has a problem of restriction feeling.

An example of a non-contact type blood oxygen saturation measuring device is disclosed in Japanese Unexamined Patent Application Publication (Translation of PCT Application) No. 2003-517342. This device measures blood oxygen saturation by using a white light source and a laser source, based on the laser Doppler effect of laser light scattered behind the living body surface. However, devices using this method have a complex configuration. Moreover, the method has another problem that the resultant signal is very faint.

Japanese Unexamined Patent Application Publication (Translation of PCT Application) No. 2014-527863 proposes a method of measuring heartbeat and blood oxygen saturation by using a normal camera while eliminating the influence of ambient light. With this method, however, variation in ambient light has large influence and makes it difficult to measure heartbeat and blood oxygen saturation stably with a high level of accuracy.

As described above, the conventional non-contact type methods to measure blood oxygen saturation have problems with accuracy and stability. None of non-contact type method to measure blood oxygen saturation is provided for practical use at this time.

On the other hand, many methods of estimating human psychological changes using thermography have been proposed (for example, see Japanese Unexamined Patent Application Publication Nos. 6-54836 and 2008-237244). These methods use thermography to detect a decrease in body temperature at the nose portion. In the human nose portion, there are many arteriovenous anastomoses, and the blood circulation is subject to interruption by the influence of the autonomic nervous system. Psychological changes, such as feeling stressed or nervous, reduce the blood flow in the nose portion under the influence of the autonomic nervous system, thus lowering the temperature at the nose portion. The apparatuses disclosed in the Japanese Unexamined Patent Application Publication Nos. 6-54836 and 2008-237244 detect changes in temperature by thermography to estimate psychological changes of the subject. The methods using thermography have slow responsiveness since the nose portion takes long to decrease in temperature. Moreover, the methods have disadvantages including the influence of the environmental temperature.

It is thought that if the blood flow in the face surface is measured accurately, it is possible to establish a method of estimating psychological changes which is highly responsive and is not influenced by the environmental temperature.

Figure 2:
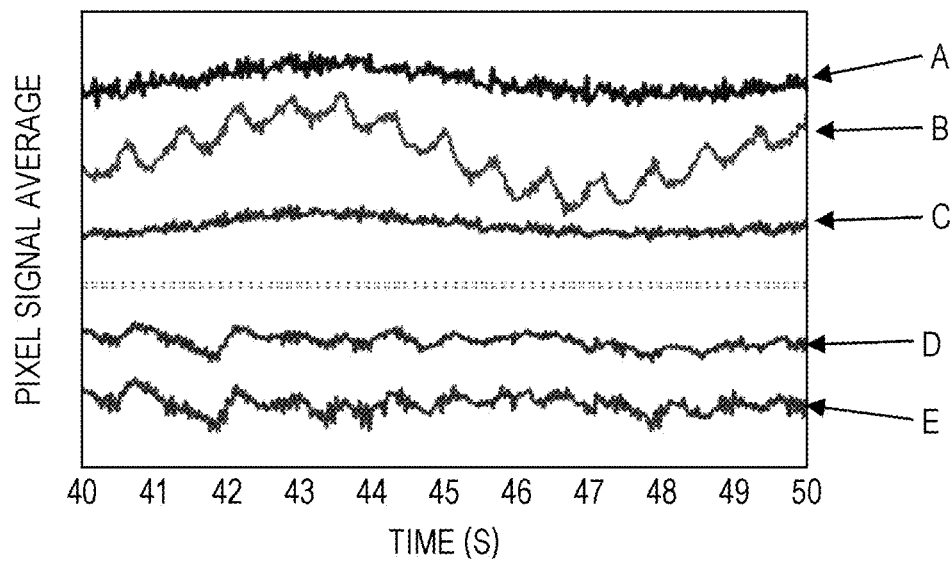
FIG. 2 is a diagram for explaining characteristics of biological information acquired by the camera for each wavelength.

Among the above-described methods, the method using a normal camera is the most promising since the method has advantages including low cost, quick response, and high resolution. Since the method using a normal camera has a problem with stability of measurement, the way of detecting biological information stably with a high level of accuracy using a normal camera is examined. First, images of a human face are taken using a normal color camera sensitive to visible light and a near-infrared camera sensitive to near infrared light, and pixel regions corresponding to a forehead portion are extracted for measurement of the average of pixel signals of each color. With the color camera, signals of three colors, including blue, green, and red, are obtained, and with the near-infrared camera, signals for wavelengths of 750 nm and 850 nm are obtained. FIG. 2 illustrates the average of signal values for each color, of the pixels in the forehead portion. In FIG. 2, signals A, B, C, D, and E indicate blue, green, red, 750 nm wavelength, and 850 nm wavelength signals, where the heart rate of the subject measured with a contact-type pulse oximeter is 80 beats per minute (0.75 seconds per beat) when the images are taken. The green signal has a distinct period of 0.75 seconds corresponding to the heart rate. However, the red and blue signals do not provide signals corresponding to the heart rate. Compared with the red and blue signals, the signals of near-infrared light with wavelengths of 750 and 850 nm include faint traces of heartbeat signals. It is therefore possible to acquire the frequency corresponding to the heartbeat by accumulating the signals of near-infrared light with wavelengths of 750 and 850 nm in a certain period of time for a frequency analysis. A method of measuring heart rate using near-infrared light in such a manner is actually proposed. However, it is difficult for the method using near-infrared light to improve in measurement accuracy because of the low signal-to-noise ratio as apparent from the signal waveforms in FIG. 2. As the technique to acquire biological information using a camera, therefore, the method using green signals obtained with a visible camera has become mainstream. Selectively using green signals improves the signal-to-noise ratio, so that the biological information can be acquired with a high level of accuracy. However, the method using green signals has a problem. There is a demand for acquiring biological information in dark places for bedtime monitoring (monitoring of infants or elderly people, monitoring of inpatients, monitoring of patients with sleep apnea syndrome, and the like), car driver monitoring, and the like. However, acquisition of biological information using green signals is not suitable for such a purpose. This is because green signals cannot be acquired in dark places. Moreover, it is difficult for the method using green signals to stably measure biological information under the conditions that the environmental light varies.

The inventor focused the aforementioned problems and examined the configuration to solve the problems. Use of near-infrared light, which is invisible to human eyes, is desirable in terms of measurement at night or in dark places. However, as illustrated in FIG. 2, when a near-infrared image is just used, only signals with a low signal-to-noise ratio are provided, and it is difficult to obtain adequate measurement accuracy. An aspect of the present disclosure relates to a method to improve the signal quality by using a pattern of near-infrared illumination to spatially separate biological information. Another aspect of the present disclosure relates to acquiring a near-infrared image using a light source that projects a pattern of near-infrared light onto the surface of a living body, simultaneously acquiring a visible light image not including near-infrared light, and carrying out an operation for both the near-infrared and visible light images to acquire biological information.

(Principle)

Hereinafter, a description is given of the principle of a biological information detection apparatus able to provide highly accurate biological information. The biological information detection apparatus according to an aspect of the present disclosure includes a near-infrared pattern illumination, a near-infrared imaging system, and a visible imaging system. The biological information detection apparatus performs proper operation for signals from the both imaging systems to implement stable biological information sensing independently of the environment. In a stable and bright illumination environment, the proportion of signals from the visible imaging system is increased. Under unstable illumination conditions or dark illumination conditions, the proportion of signals from the near-infrared imaging system is increased. This configuration can implement stable biological information sensing independently of the environment.

FIG. 1A is a diagram illustrating a schematic configuration of a biological information detection apparatus of an illustrative embodiment of the present disclosure. The biological information detection apparatus includes a light source 1, which projects near-infrared light L0 onto an object including a living body, and cameras 201 and 202 as the imaging systems. Herein, the camera 201 takes an image of near-infrared light while the camera 202 takes an image of visible light. In FIG. 1A, a dot array pattern including plural dot images discretely arrayed is projected onto a living body 3 as the near-infrared pattern. The light source 1, which projects near-infrared light, is placed so as to project plural dot images onto the living body 3. The cameras 201 and 202 include image sensors and take images of a body surface 4. The cameras 201 and 202 generate and output image signals. The camera 202 takes an image of reflection light L3 in the visible wavelength range from the living body 3.

FIG. 1A illustrates the structure of the skin surface of the living body 3 as an object. Surface reflected light, which is reflected on the body surface 4, keeps the dot array pattern from the light source 1. On the contrary, internal scattered light, which enters into the living body 3, scatters within the living body 3, and exits through the body surface 4, loses the dot array pattern from the light source 1 due to strong scattering within the living body 3. By using the light source 1, which projects the dot array pattern, the surface reflected light L1 is spatially separated from the internal scattered light L2 easily.

The living body 3 illustrated in FIG. 1A is human skin and includes epidermis 33, dermis 34, and subcutaneous tissue 35. The epidermis 33 does not include vessels. The dermis 34 includes capillaries 31 and arterioles and venules 32. Since the epidermis 33 does not include vessels, the surface reflected light L1 does not include information concerning blood. The epidermis 33 includes melanin pigment, which strongly absorbs light. The surface reflected light L1 from the epidermis 33 is therefore considered as noise in acquiring blood information. The surface reflected light L1 is not only less useful in acquiring blood information but also prevents acquisition of accurate blood information. In order to detect biological information with a high level of accuracy, it is important to reduce the influence of the surface reflected light and acquire information of the internal scattered light efficiently.

Figure 1B:
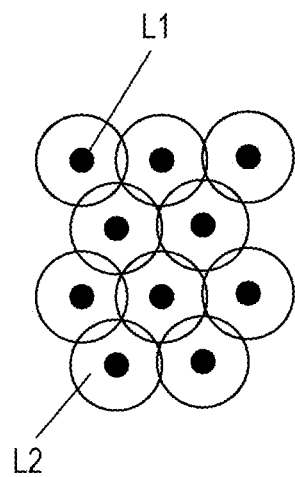
FIG. 1B is a diagram for explaining characteristics of an image of the body surface captured with a camera.

An embodiment of the present disclosure has a novel configuration which spatially separates the surface reflected light from the internal scattered light using the light source 1, which projects a near-infrared pattern, and the camera 201, which takes an image of near-infrared light. This allows highly accurate non-contact measurement of information within the living body. FIG. 1B is a schematic diagram for explaining the two-dimensional distribution of an image outputted from the camera 201. The plural dot images which are discretely arrayed and are projected by the light source 1 are represented by black circles. The surface reflected light is reflected on the black circles in the skin surface. On the other hand, the internal scattered light spreads within the skin to the outside of each of the black circles. The distribution of the internal scattered light is represented by white circles in FIG. 1B. The surface reflected light and the internal scattered light are easily separated based on the image taken by the camera 201. In the two-dimensional image, the black circle regions of high light intensity are regions where the surface reflected light is mainly included, and regions other than the black circles are the regions where the internal scattered light is mainly included. By using the light source projecting a pattern in such a manner, the surface reflected light is easily separated from the internal scattered light.

One of the conventionally used methods to separate the surface reflected light which is reflected on the body surface uses polarized illumination as disclosed in Japanese Unexamined Patent Application Publication No. 2002-200050, for example. The method using polarized illumination employs a polarizer with the transmission axis set orthogonal to the polarization direction of the illumination light reflected on the target. By taking an image with a camera through the polarizer, the influence of the surface reflected light can be reduced. For reflection on rough surfaces, including skin, the method using polarized illumination cannot separate the surface reflected light sufficiently because the polarization degree of the surface reflected light varies from position to position. Moreover, since skin is a strong scatterer, light scattered and reflected in shallow part of the skin surface does not include blood information and needs to be separated. However, polarization is lost in shallow part of skin, and the component scattered and reflected in the shallow part cannot be separated. Accordingly, the signal-to-noise ratio cannot be improved. According to the method of the present disclosure, light scattered in shallow part of skin is located around dot images of the near-infrared pattern of the light source and can be therefore easily separated spatially from light which is reflected from deep part of the skin and includes biological information. According to the method of the present disclosure, the surface reflected light is spatially separated from the internal scattered light, so that the influence of the surface reflected light is effectively reduced.

In the biological information detection apparatus of each embodiment of the present disclosure, the wavelength of light from the light source that projects a dot array pattern is also important. The wavelength of light from the light source can be set to not less than substantially 650 nm and not greater than substantially 950 nm, for example. This wavelength range is included in the red to near-infrared wavelength range. In this specification, not only visible light but also near-infrared light is referred to using a term "light". The aforementioned wavelength range is called a "near-infrared window" and is known for low absorptivity within the body.

Figure 3:
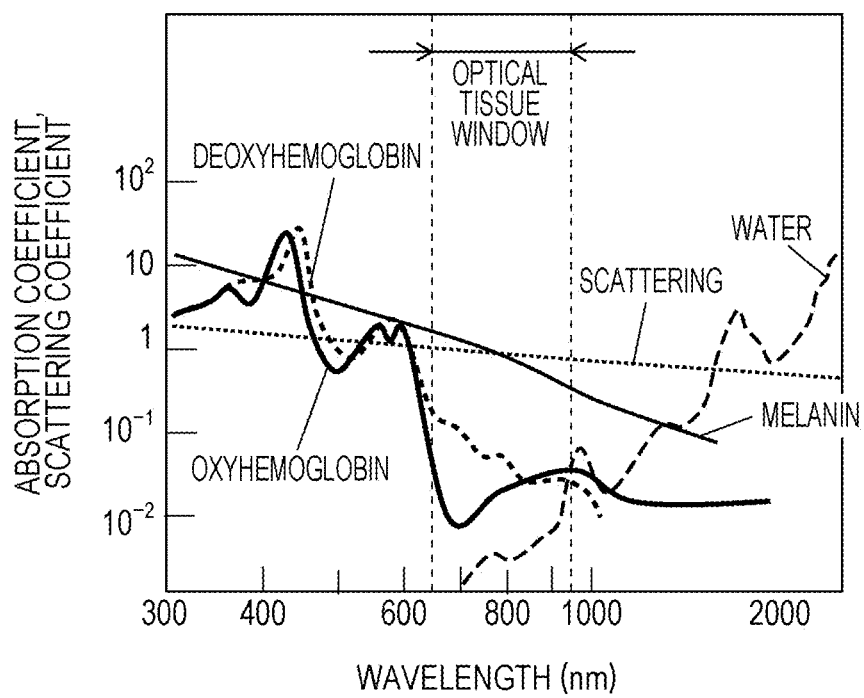
FIG. 3 is a diagram illustrating absorption coefficients and scattering coefficients of hemoglobin, melanin, and water, which are main components of a living body, for visible to near-infrared light.

FIG. 3 is a diagram illustrating wavelength dependences of absorption coefficients of oxyhemoglobin, deoxyhemoglobin, melanin, and water and scattering coefficients thereof within the body. Blood that is hemoglobin absorbs a lot of light in the visible wavelength range less than 650 nm while water absorbs a lot of light in a wavelength range greater than 950 nm. Accordingly, light in these wavelength ranges is not suitable for acquisition of information within the living body. On the other hand, in a wavelength range not less than substantially 650 nm and not greater than substantially 950 nm, the absorption coefficients of hemoglobin and water are comparatively low, and the scattering coefficients thereof are comparatively high. Accordingly, light in this wavelength range having entered the body is strongly scattered and returned to the body surface. It is therefore possible to acquire information within the body efficiently.

The biological information detection apparatus of embodiments of the present disclosure utilizes light in a wavelength range corresponding to the "near-infrared window". The biological information detection apparatus therefore highly-accurately separates and detects the light reflected on the body surface from the light returned after scattering within the body, so that information within the body can be acquired efficiently.

By using near-infrared light, the biological information detection apparatus of embodiments is able to stably acquire biological information in various situations, including at night, compared with the conventional methods using visible light. However, the method using near-infrared light has difficulties in some cases where measurement is performed in the environment of sunlight illumination or lamp illumination. The sunlight and lamp light include a lot of near-infrared light in addition to visible light. When the near-infrared pattern is projected in such an environment, near-infrared light from the sunlight or lamp light in the environment is also projected onto the target including part other than the regions where the dots of the near-infrared pattern are projected. Even in such a case, the surface reflected light could be separated from the internal scattered light based on the two-dimensional distribution in the taken image. However, there is a concern that the measurement accuracy could be reduced due to the signal-to-noise ratio reduced by the influence of the sunlight or lamp light. In this case, the measurement accuracy can be improved by using visible light signals which are simultaneously acquired from the camera 202. As described above, in the environment of bright and stable illumination, a high level of measurement accuracy can be implemented by using green signals. On the other hand, in dark places, a high level of measurement accuracy can be implemented by using near-infrared light. Physiological information can be therefore stably acquired in various environments by switching or using together the near-infrared information and visible light information for calculation in accordance with the measurement environment. In bright stable ambient light, use of green signals allows stable measurement. In such an environment, near-infrared illumination may be turned off. This can reduce power consumption for illumination, thus implementing energy-saving measurement.

The present disclosure includes the following items, for example.

[Item 1]

A biological information detection apparatus according to Item 1 of the present disclosure includes:

a light source which projects a pattern of near-infrared light onto an object including a living body;

an imaging system which includes first photodetector cells detecting light in a near-infrared wavelength range and second photodetector cells detecting light in a visible wavelength range, and generates a first image signal representing a first image, and a second image signal representing a second image; and a calculator which calculates biological information concerning the living body using at least one selected from the group consisting of the first and second image signals. The first image is an image of the object on which the pattern is projected, the image taken in the near-infrared wavelength range. The second image is an image of the object taken in the visible wavelength range.

[Item 2]

In the biological information detection apparatus according to Item 1, the pattern may include a plurality of dots.

[Item 3]

In the biological information detection apparatus according to Item 1 or 2, the near-infrared light may include light with wavelengths of not less than 650 nm and not greater than 950 nm, and the light in the visible wavelength range may include light with wavelengths of not less than 500 nm and not greater than 620 nm.

[Item 4]

In the biological information detection apparatus according to any one of Items 1 to 3, the biological information may include at least one selected from the group consisting of a heart-beat rate of the living body, a blood pressure of the living body, a blood flow of the living body, a blood oxygen saturation level of the living body, a melanin concentration in skin of the living body, information whether or not there is a spot in the skin of the living body, and information whether or not there is a bruise in the skin of the living body.

[Item 5]

In the biological information detection apparatus according to any one of Items 1 to 4, the calculator may detect a first portion corresponding to the living body in the first image using the first image signal.

[Item 6]

In the biological information detection apparatus according to Item 5, the calculator may determine whether the living body is present at the position corresponding to a pixel included in the first image based on a ratio of a variation of an intensity of the first image signal corresponding to the pixel and an intensity of the first image signal corresponding to each of pixels around the pixel to an average of the intensity of the first image signal corresponding to the pixel and the intensity of the first image signal corresponding to each of the pixels around the pixel.

[Item 7]

In the biological information detection apparatus according to Item 5 or 6, the calculator may calculate the biological information based on a ratio of a first intensity average to a second intensity average, the first intensity average may be an average of intensities of the first image signal corresponding to some pixels selected, in descending order of intensities of the first image signal, from a pixel included in the first portion of the first image and pixels arranged around the pixel, and the second intensity average may be an average of intensities of the first image signal corresponding to other pixels selected, in ascending order of intensities of the first image signal, from the pixel and the pixels arranged around the pixel.

[Item 8]

In the biological information detection apparatus according to Item 5 or 6, the calculator may calculate the biological information using an average of intensities of the second image signal corresponding to pixels included in a second portion of the second image, the second portion corresponding to the first portion in the first image.

[Item 9]

In the biological information detection apparatus according to any one of Items 1 to 8, the imaging system may further include:

an image sensor including an imaging surface divided into a first region where the first photodetector cells are arranged and a second region where the second photodetector cells are arranged;

a first optical system forming the first image in the first region; and a second optical system forming the second image in the second region.

[Item 10]

In the biological information detection apparatus according to Item 9, the imaging system may further include:

a first band-pass filter transmitting light in the near-infrared wavelength range; and a second band-pass filter transmitting light in the visible wavelength range.

[Item 11]

In the biological information detection apparatus according to Item 9, the imaging system may further include:

a first band-pass filter transmitting light in the near-infrared wavelength range;

a linear polarization filter; and a second band-pass filter transmitting light in the visible wavelength range, the near-infrared light may be linearly polarized, and the linear polarization filter may be positioned so that a polarization direction of linearly polarized light transmitted by the linear polarization filter is perpendicular to a polarization direction of the near-infrared light.

[Item 12]

In the biological information detection apparatus according to Item 9, the image sensor may include:

a first color filter which faces the first photodetector cells and transmit light in the near-infrared wavelength range;

a second color filter which faces the second photodetector cells and transmit light in the visible wavelength range; and a near-infrared absorption filter which faces the second photodetector cells and the second color filter, and absorbs the light in the near-infrared wavelength range.

[Item 13]

In the biological information detection apparatus according to any one of Items 1 to 8, the imaging system may include a first imaging sub-system and a second imaging sub-system, and the first imaging sub-system may include:

a first image sensor including a first imaging surface in which the first photodetector cells are arranged; and a first optical system forming the first image on the first imaging surface, and the second imaging sub-system may include:

a second image sensor including a second imaging surface in which the second photodetector cells are arranged; and a second optical system forming the second image on the second imaging surface.

[Item 14]

In the biological information detection apparatus according to Item 13, the first imaging sub-system may include a first band-pass filter transmitting light in the near-infrared wavelength range, and the second imaging sub-system may include a second band-pass filter transmitting light in the visible wavelength range.

[Item 15]

In the biological information detection apparatus according to any one of Items 1 to 14, the calculator may calculate a blood flow of the living body and a blood oxygen saturation level of the living body based on the first and second imaging signals, and may generate information representing at least one selected from the group consisting of physical condition, emotion, and concentration of the living body based on the blood flow of the living body and the blood oxygen saturation level of the living body.

[Item 16]

In the biological information detection apparatus according to any one of Items 1 to 14, when the first and second images each include at least one selected from the group consisting of a cheek and a nose of the living body, the calculator may calculate a change in a blood flow with time and a change in a blood oxygen saturation level with time in the at least one selected from the group consisting of the cheek and the nose using the first and second image signals, and may generate information representing at least one selected from the group consisting of physical condition, emotion, and concentration of the living body using the change in the blood flow with time and the change in the blood oxygen saturation level with time.

[Item 17]

In the biological information detection apparatus according to any one of Items 1 to 14, when the first and second images each include a cheek and a nose of the living body, the calculator may calculate a change in a blood flow with time and a change in a blood oxygen saturation level with time in the cheek and a change in a blood flow with time and a change in a blood oxygen saturation level with time in the nose, and based on comparison between the change in the blood flow with time and the change in the blood oxygen saturation level with time in the cheek and the change in the blood flow with time and the change in the blood oxygen saturation level with time in the nose, may generate information representing at least one selected from the group consisting of physical condition, emotion, and concentration of the living body.

[Item 18]

In the biological information detection apparatus according to any one of Items 1 to 17, the imaging system may further include:

an image sensor including an imaging surface in which the first photodetector cells are arrayed;

an optical system forming the first image on the imaging surface; and an adjustment mechanism adjusting the focal point of the optical system, in which the adjustment mechanism adjusts a focal point so as to maximize contrast of the first image.

[Item 19]

In the biological information detection apparatus according to Item 1, the calculator may perform an operation for comparison between reliability of the biological information calculated using the first image signal and reliability of the biological information calculated using the second image signal.

[Item 20]

In the biological information detection apparatus according to any one of Items 1 to 8, the imaging system may further include an image sensor including an imaging surface which is divided into a first region where the first photodetector cells are arranged and a second region where the second photodetector cells are arranged;

a projection optical system forming an image in the first and second regions; and a reflection optical system which brings the light in the near-infrared wavelength range and the light in the visible wavelength range incident on the projection optical system.

In the present disclosure, all or a part of any of circuit, unit, device, part or portion, or any of functional blocks in the block diagrams may be implemented as one or more of electronic circuits including, but not limited to, a semiconductor device, a semiconductor integrated circuit (IC) or an LSI. The LSI or IC can be integrated into one chip, or also can be a combination of plural chips. For example, functional blocks other than a memory may be integrated into one chip. The name used here is LSI or IC, but it may also be called system LSI, VLSI (very large scale integration), or ULSI (ultra large scale integration) depending on the degree of integration. A Field Programmable Gate Array (FPGA) that can be programmed after manufacturing an LSI or a reconfigurable logic device that allows reconfiguration of the connection or setup of circuit cells inside the LSI can be used for the same purpose.

Further, it is also possible that all or a part of the functions or operations of the circuit, unit, device, part or portion are implemented by executing software. In such a case, the software is recorded on one or more non-transitory recording media such as a ROM, an optical disk or a hard disk drive, and when the software is executed by a processor, the software causes the processor together with peripheral devices to execute the functions specified in the software. A system or apparatus may include such one or more non-transitory recording media on which the software is recorded and a processor together with necessary hardware devices such as an interface.

Hereinafter, the embodiments of the present disclosure are described in more detail. The following embodiments relate to biological information detection apparatuses which mainly measure biological information in a non-contact manner from a human face surface as the body surface. The technique of the present disclosure is applicable not only to human face surfaces but also to body sites other than face surfaces or animals other than human beings.

(Embodiment 1)

As a first embodiment, a description is given of a system for non-contact heartbeat measurement to which the technique of the present disclosure is applied. With increasing healthcare interest, constant biological information sensing is increasingly important. Systems able to constantly measure biological information in non-contact manner are important not only in hospitals but also for healthcare in daily life. The system of Embodiment 1 is able to monitor heart rate and heart rate variability in a non-contact manner.

FIG. 4A is a diagram illustrating a schematic configuration of a biological information detection apparatus of Embodiment 1. As illustrated in FIG. 4A, the biological information detection apparatus of Embodiment 1 includes a light source 1, a camera 201, a camera 202, and a computer 20. The light source 1 is provided at a distance from living body 3 and projects rays of light in the near-infrared wavelength range. The camera 201 is able to record an image of a body surface irradiated and takes an image of near-infrared light. The camera 202 is adjusted so as to have the substantially same range of imaging as that of the camera 201 and takes an image of visible light. The computer 20 calculates biological information from the taken image and outputs the biological information. The cameras 201 and 202 correspond to the imaging systems. The computer 20 includes a calculator.

The light source 1, which projects a near-infrared pattern, is designed to project a dot array pattern onto the body surface. The dot array pattern is typically a set of minute bright dots two-dimensionally arranged. The dot array pattern may be a set of minute bright dots one-dimensionally arranged in accordance with the intended use. In Embodiment 1, the light source 1 may be a random dot array pattern laser projector RPP017ES (OSELA INC.), for example. This laser light source emits a 830 nm near-infrared laser beam and projects a laser dot array pattern of 57446 dots in an angle of view of 45°×45°.

The camera 201 includes a lens 501 as a first optical system and a casing 601. The lens 501 can be an assembly of plural lenses. In the casing 601, an image sensor 701 and a band-pass filter 801 are provided. The image sensor 701 is a solid-state image sensor. The band-pass filter 801 transmits only light with wavelengths of 830±10 nm. The image sensor 701 receives near-infrared light. On the other hand, similar to the camera 201, the camera 202 includes a lens 502 as a second optical system, a casing 602, an image sensor 702, and a band-pass filter 802. The band-pass filter 802 transmits green light with wavelengths of 520 to 600 nm. The image sensor 702 receives visible light.

Figure 4B:
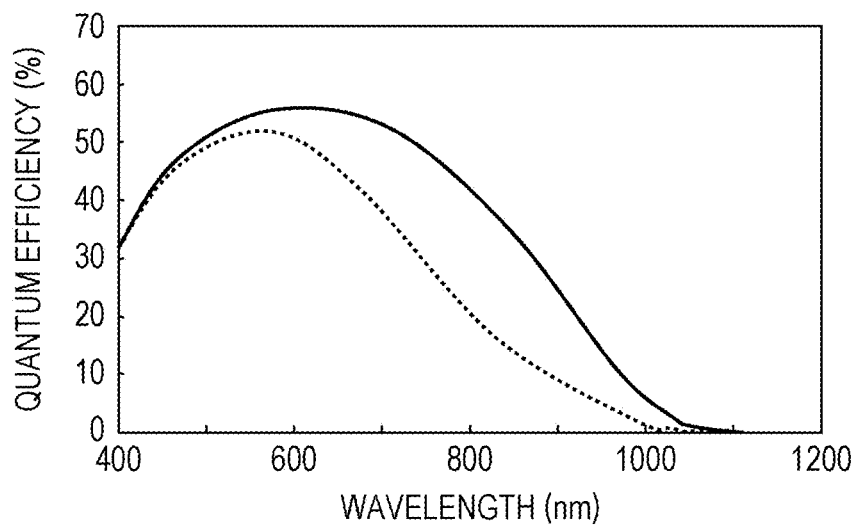
FIG. 4B is a diagram illustrating characteristics of a near-infrared image sensor of Embodiment 1.

FIG. 4B illustrates the characteristics of the image sensors 701 and 702 with solid lines. In Embodiment 1, the image sensors 701 and 702 are both monochrome silicon image sensors that do not include color filters and are sensitive to ultraviolet to near-infrared light (wavelength: 300 to 1200 nm). A normal monochrome silicon image sensor has peak sensitivity at a wavelength of about 550 to 600 nm as indicated by a dot line in FIG. 4B. On the other hand, the image sensors 701 and 702 in Embodiment 1 are image sensors which have sensitivity in the substantially same wavelength range as that of normal monochrome silicon image sensors and are designed to have deeper photodiodes to be more sensitive to light with longer wavelengths. The image sensors having these characteristics are referred to as near-infrared image sensors in the specification. In order to detect near-infrared light signals with higher sensitivity, not only the image sensor 701 but also the image sensor 702 is composed of a near-infrared image sensor in Embodiment 1. Using the two image sensors having the same characteristics facilitates the subsequent signal processing. The image sensor 702 may be composed of a low-cost normal monochrome image sensor.

Figure 4C:
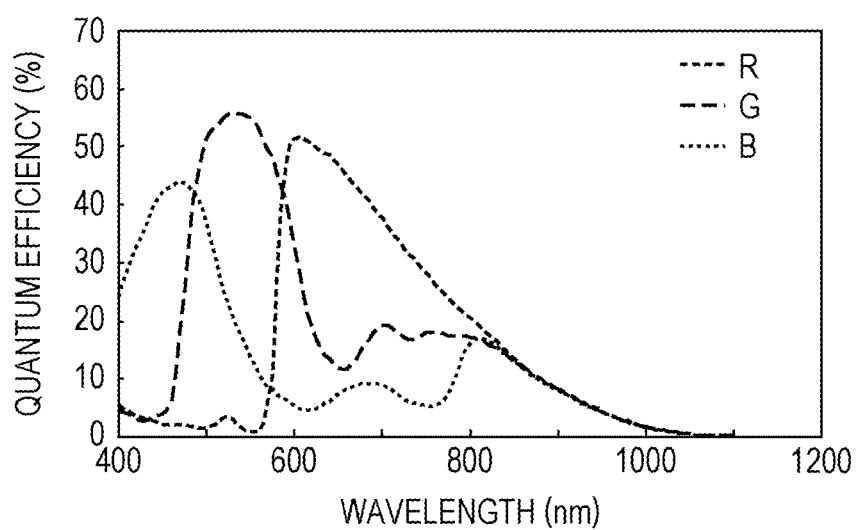
FIG. 4C is a diagram illustrating characteristics of a color image sensor of Embodiment 1.

The image sensor 702 may be composed of a normal color image sensor illustrated in FIG. 4C. The color image sensor includes red, green, and blue color filters on pixels to separately detect three color signals. In this case, it is necessary to extend the range of transmission wavelength of the band-pass filter 802, which is provided in front of the image sensor 702, by about 400 to 650 nm to enable transmission of light in the entire visible wavelength range. As already described, use of green light is effective for sensing of biological information, and it is thought that pixels for blue and red light are unnecessary. However, in order to correct the motion (body motion) of the subject, as described later, it is effective to perform operation using green signals including a lot of biological information and red or blue signals not including biological information. Accordingly, in the situation where the body moves significantly, use of the color image sensor illustrated in FIG. 4C is effective.

When the subject is a human being, as illustrated in part (a) of FIG. 4A, the camera 201 acquires an image including plural dot images having brightness corresponding to the infrared reflectivity which varies from position to position. As already described, the living body includes a specific optical property called the "near-infrared window" for wavelengths of red to near-infrared light. The human body skin has a small absorption coefficient and a large scattering coefficient in this wavelength range. Accordingly, light transmitted through the skin surface is repeatedly subject to multiple scatter within the body to be diffused to a wide range and exits from the skin surface. Living bodies are characterized in that the proportion of the internal scattered light is higher than that of the surface reflected light in the aforementioned wavelength range. In objects other than living bodies, the proportion of the surface reflected light is higher than that of the internal scattered light. Accordingly, a living body can be detected based on the ratio of the surface reflected light to the internal scattered light, so that the region (a human body region) corresponding to the living body in the image can be detected. Moreover, biological information can be acquired rapidly by using pixel signals only in the obtained human body region of the image. This is because the human body region can be detected using the optical property of skin, more rapidly with a higher level of accuracy than methods using conventional image recognition. Herein, as illustrated in part (b) of FIG. 4A, a forehead portion (indicated by a rectangular frame), in which stable biological information can be acquired, is extracted from the detected human body region for use in detection of biological information. Since the camera 202 is adjusted so as to have the substantially same range of imaging as the camera 201, the forehead position in the camera 202 can be determined from the coordinates of the forehead region obtained by the camera 201. In the process of detecting biological information from a visible image, signals in the forehead region are used. Herein, since the near-infrared image and visible image are of an identical subject, the forehead position is determined in the visible image with a high level of accuracy by image recognition for the green image. However, image recognition has large computational burden and is desirably simplified. In the near-infrared image, the biological information detection region is detected rapidly with a high level of accuracy based on the internal scattered light component and surface reflected light component. The biological information detection region in the green image can be determined by using this image signal. When the positions of the two cameras are adjusted with a sufficiently high level of accuracy, the biological information detection region in the green image is determined by shifting the coordinates of the biological information detection region in the near-infrared image by a certain value. When the positions of the two cameras are not adjusted adequately, the biological information detection region in the green image can be determined by performing AND operation for the biological information detection region obtained from the near-infrared image and a region where the reflected light intensity is not less than a threshold in the green image.

As illustrated in part (c) of FIG. 4A, the surface reflected light L1 and internal scattered light L2 are spatially separated in the near-infrared image acquired with the camera 201 and are both used to calculate biological information. On the other hand, biological information is calculated from the green image acquired with the camera 202. As already described, biological information is stably acquired in various environments by switching or using together the near-infrared information and visible light information in accordance with the measurement environment.

Figure 4D:
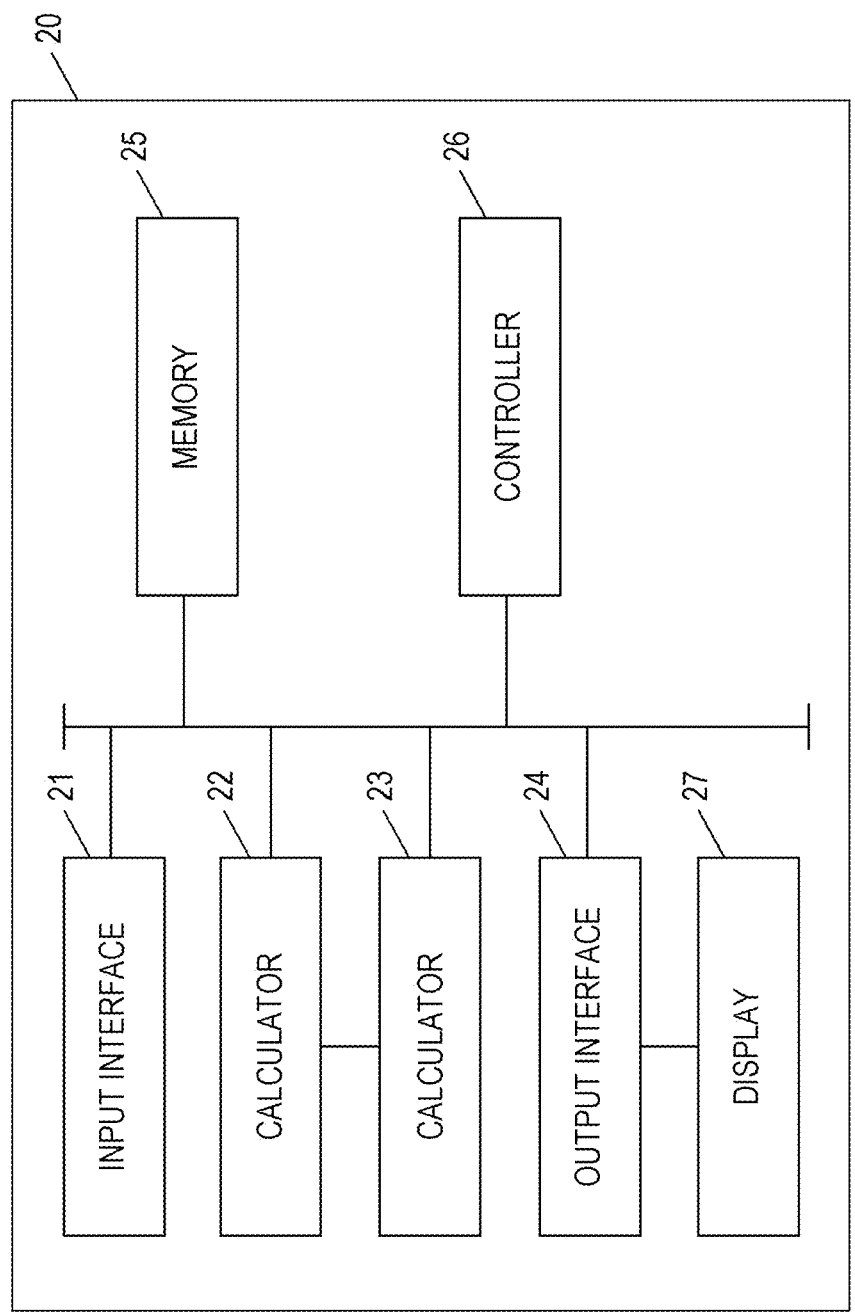
FIG. 4D is a block diagram illustrating the configuration of a computer of Embodiment 1.

FIG. 4D is a block diagram illustrating the configuration of the computer 20 as the biological information calculation apparatus. The computer 20 includes an input interface 21, a calculator 22, a calculator 23, a memory 25, a controller 26, an output interface 24, and a display 27. The input interface 21 is electrically connected to the cameras 201 and 202. The calculator 22 performs signal processing to detect a region corresponding to a human body in an image. The calculator 23 uses image data in the detected human body region to calculate biological information. The memory 25 records various data. The controller 26 controls operations of the entire apparatus. The output interface 24 outputs data. The display 27 displays processing results. The calculators 22 and 23 may be image-processing circuits such as digital signal processors (DSPs), for example. The controller 26 may be an integrated circuit such as a central processing unit (CPU) or a microcomputer, for example. The controller 26 executes a control program recorded in the memory 25, for example, to perform controls including: instructing the light source 1 to be turned on, instructing the cameras 201 and 202 to take images, and instructing calculators 22 and 23 to perform calculation. The controller 26 and calculators 22 and 23 may be integrated as a single circuit. Although the computer 20 includes the display 27 in this example, the display 27 may be an external device electrically connected by wire or wirelessly. The computer 20 may acquire image information from a remote camera by a not-illustrated communication circuit.

Figure 5A:
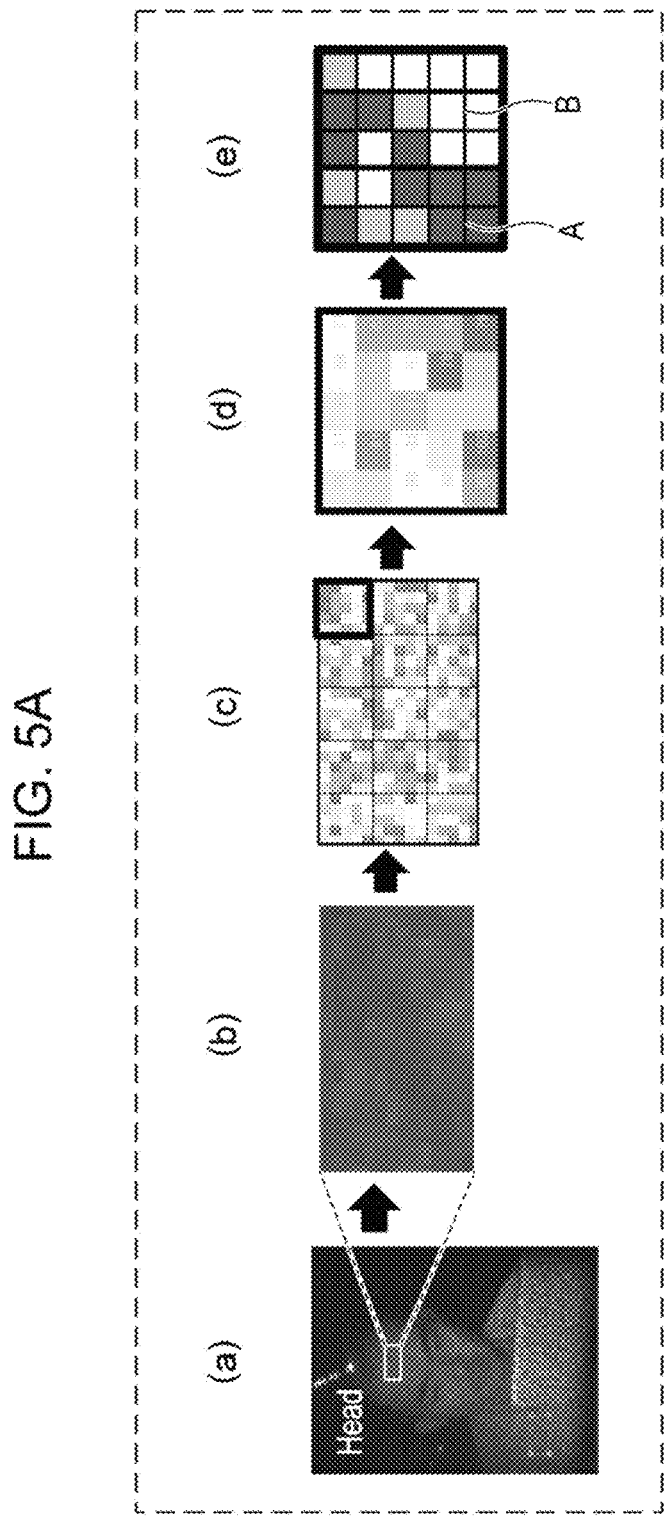
FIG. 5A is an explanatory diagram schematically illustrating a flow of signal processing of Embodiment 1.

Herein, a description is given of the method using the light source 1 projecting a near-infrared pattern and the effect thereof. As illustrated in FIG. 2, there has been a problem that the biological information acquired from the near-infrared image taken using a uniform near-infrared light source hardly has sufficient accuracy because of the low signal-to-noise ratio thereof. In the present disclosure, the light source projects a near-infrared pattern. As already described, the surface reflected light, which is directly reflected on the living body surface, and the internal scattered light, which enters the living body, scatters within the body, and exits from the surface, can be spatially separated easily in the image taken by capturing with a camera, reflection of the near-infrared pattern from the living body surface. The surface reflected light does not include information within the living body while the internal scattered light, which scatters within the skin and is radiated again, includes information within the living body. Accordingly, by selectively using the internal scattered light, biological information can be detected with a high level of accuracy. A description is given of a concrete detection method in detail using FIGS. 5A, 5B, and 5C. Part (a) of FIG. 5A is an image of a human body taken with a near-infrared camera, the human body on which near-infrared pattern illumination composed of a random dot array pattern is projected. Herein, a forehead region, in which biological information is expected to be detected stably, is selected for acquisition of biological information. The human body region is extracted and defined in the near-infrared image for calculation. In the image of the forehead region illustrated in part (b) of FIG. 5A, contrasts corresponding to the illumination pattern are discriminated. As illustrated in part (c) and part (d) of FIG. 5A, the forehead region is divided into plural sections, each including 5 by 5 pixels. As illustrated in part (e) of FIG. 5A, for each section, light intensity is compared between 25 pixels, and the ten highest light intensities (corresponding to the pixels indicated by A) are averaged. The result is defined as the intensity of the surface reflected light component in the section of interest. On the other hand, the ten lowest light intensities (corresponding to the pixels indicated by B) among 25 pixels are averaged. The result is defined as the intensity of the internal scattered light component in the section of interest. The intensity of the surface reflected light component and the intensity of the internal scattered light component are calculated for every section of 25 pixels in the entire forehead region. The calculated intensities of the surface reflected light component and internal scattered light component are individually averaged as the average intensity of the surface reflection light component and the average intensity of the internal scattered light component in the forehead region, respectively. Herein, the surface reflected light and internal scattered light include information of spatially close pixels and produce similar signals. Disturbance factors (fluctuations in environmental light and motions of the measurement system and subject), which will always become significant problems in non-contact biological information sensing, influence the surface reflected light and internal scattered light to the substantially same extent. The only difference therebetween is that the internal scattered light includes more information within the living body. By using this characteristic, the disturbance factors included in the process of signal detection, such as body motion, can be corrected. Concrete correcting methods include using the intensity ratio of the internal scattered light to the surface reflected light or reducing the intensity of the surface reflected light multiplied by a constant from the intensity of the internal scattered light. The constant to be multiplied with the intensity of the surface reflected light may be calculated by the independent component analysis. In Embodiment 1, the disturbance factors are corrected by dividing the intensity of the internal scattered light by the intensity of the surface reflected light because such simple division provides a sufficient effect of correction. The effect of correction is illustrated in FIG. 5B. FIG. 5B illustrates, with respect to time, signal A indicating the average of all the pixels in the forehead region and signal B indicating the intensity ratio of the internal scattered light to the surface reflected light which is calculated by the method illustrated in FIG. 5A. In FIG. 5B, the subject is at rest, and after 35 seconds, the subject starts shaking his/her head. The measurement is performed by following the forehead region so that the forehead region be the measurement region. The intensity average of all the pixels varies significantly due to shaking of the head, showing that it is difficult to detect small signals of heartbeat that look like fluctuations. On the other hand, although the intensity ratio of the internal scattered light to the surface reflected light shows an influence of shaking the head, the output signal shows definite signals of pulsation, and it is revealed that the biological information can be detected irrespectively of the significant body motion. FIG. 5C illustrates the obtained signals of heartbeat. Signal A, which is obtained by the conventional method using all the pixels, has a low signal-to-noise ratio of the heartbeat information. It is therefore difficult to obtain biological information stably. Signal B, which is obtained by using the near-infrared pattern light source to separate and measure the internal scattered light and surface reflected light, followed by signal operation, has a signal-to-noise ratio considerably improved. In the example illustrated in FIG. 5C, the signal-to-noise ratio is 30 times higher than that in the case of using the average of all the pixels. The method using the near-infrared pattern light source is very effective to detect biological information using near-infrared light. The aforementioned example uses 5 by 5 pixels, ten pixels having the highest light intensities, and ten pixels having the lowest light intensities. The optimal values thereof vary depending on the resolutions of the light source pattern and cameras, the distance between the subject and cameras, or the like. Accordingly, it is preferable that these values are variably set in accordance with the system and usage conditions.

Hereinabove, the signal processing in the biological information sensing using the near-infrared pattern light source and near-infrared camera is described. In the biological information sensing using green light, as already described, it is unnecessary to use a special light source because of the high signal-to-noise ratio of green light. The biological information sensing can be implemented using environmental light as the light source. Accordingly, the operation in the signal processing for green light can be easily performed by using the average light intensity in the determined measurement region after the measurement region (the forehead region, for example) is determined. However, the average light intensity is strongly influenced by body motion even in the case of green light. For stable signal detection, green signals may be also subjected to body motion correction. The influence of body motion can be removed by operation using image data including a small amount of biological information and image data including a large amount of biological information, which are of an identical subject at the same scene, as described in the body motion correction method for the near-infrared image. In the case of the near-infrared image, the surface reflected light component is used as the image data including a small amount of biological information while the internal scattered light is used as the image data including a large amount of biological information. In the case of green image, since data of the green image includes a lot of biological information, the surface reflected light component acquired from the near-infrared light is used as the image data including a small amount of biological information. The body motion correction in the green image can be implemented by performing an operation for the average light intensity of green light and the average light intensity of the surface reflected light component of the near-infrared light. Concrete calculation methods to remove the influence of body motion include dividing the average light intensity of green light by the intensity of the surface reflected light or reducing the intensity of the surface reflected light multiplied by a constant from the average light intensity of green light. This can implement highly accurate measurement. The body motion correction for green light may be performed by another method. When the image sensor 702 in the measurement system illustrated in FIG. 4A is a color image sensor, signals of three colors (red, green, and blue) are outputted from the visible camera. The body motion correction can be implemented by performing the operation using the green signal including a large amount of biological information and the red or blue signal including a small amount of biological information. This method has advantages that the variation in environmental light can be corrected as well as body motion and that the correction is performed with a high level of alignment accuracy within the same angle of view. However, the method has problems such as reduction in green signals and reduction in resolution.

Figure 6:
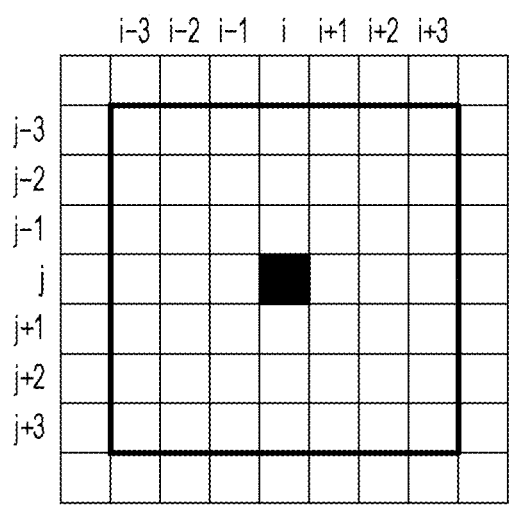
FIG. 6 is an explanatory diagram illustrating a contrast calculation method in Embodiment 1.

In the aforementioned biological information sensing, to efficiently determine the measurement region, the human body region is detected using near-infrared pattern illumination. The conventional method extracts a face part using image recognition. However, image recognition has heavy computational load, and high-speed processing requires a high-performance calculator, thus increasing the apparatus size and cost. According to an aspect of the present disclosure, use of near-infrared pattern illumination enables human body detection to be performed highly accurately and quickly with small computational load. A description is given of a concrete method of detecting a human body using FIG. 6. FIG. 6 is a diagram illustrating an example of the pixel region used for calculation of contrast in the detection region. The image data is recorded in the memory 25 as two-dimensional intensity data. $P_{ij}$ is data of a pixel located at an intersection of the i-th column in the horizontal (x) direction and the j-th row in the vertical (y) direction. Contrast $C_{ij}$ of a pixel (i, j) is defined as follows:

$$C_{ij}=S_{ij}/A_{ij}$$

Herein, $S_{ij}$ and $A_{ij}$ are the standard deviation and average of pixel data within a region of 7 by 7 pixels around a pixel (i, j), respectively. As the ratio of the internal scattered light to the surface reflected light increases, the standard deviation $S_{ij}$ degreases, and $C_{ij}$ therefore decreases. After this processing is repeatedly performed for all the pixels, the calculator 22 extracts only pixels having $C_{ij}$ within a predetermined range. As an example, in the near-infrared image illustrated in FIG. 5A, the human body region can be correctly extracted by setting $C_{ij}$ to: $0.2<C_{ij}<0.47$.

As described above, according to Embodiment 1, the human body region can be efficiently detected from the target by using the specific optical property of skin. Herein, to calculate contrast (that is, the contrast between the surface reflected light and internal scattered light) in the image, the average and standard deviation in a region of 7 by 7 pixels are calculated by way of example. The size (that is, the number of pixels) of each pixel region used to calculate the contrast is properly set in accordance with the density of the plural dot images formed by the near-infrared pattern and the resolution of the camera 202. To reduce the variation in the result of calculation, the pixel region used to calculate the contrast may include plural (three or more, for example) illuminated dot images. Increasing the number of pixels in each region used to calculate the contrast increases the accuracy of the calculated value of the contrast but reduces the resolution of the obtained living body image. Accordingly, the number of pixels in the region used to calculate the contrast is properly set in accordance with the system configuration and intended use. Moreover, the processing speed depends on not only the number of pixels in each region used to calculate the contrast but also intervals of the pixels which are subjected to the above processing. In the above processing, the calculation is performed every five pixels for speeding up the processing. Reducing the intervals of pixels subjected to the processing reduces the processing speed but increases the resolution. The intervals of pixels subjected to the processing is also properly set in accordance with the system configuration and intended use. The predetermined contrast range is not limited to $0.2<C_{ij}<0.47$ and is properly set in accordance with the system configuration and intended use.

A lot of methods have been proposed to monitor heartbeat in a non-contact manner using a normal visible camera or a near-infrared camera. With those conventional methods, the surface reflected light component is not sufficiently separated from the internal scattered light component, and it is therefore difficult to measure the heartbeat stably with a high level of accuracy because non-contact type measurement is susceptible to the influence of ambient light. According to Embodiment 1, the surface reflected light component is separated spatially from the internal scattered light component, so that the heartbeat is measured stably with a high level of accuracy. For example, when the body moves during conventional remote heartbeat measurement using a camera, the heartbeat measurement cannot be performed with a high level of accuracy due to the unstable detection. The method of Embodiment 1 provides stable heartbeat measurement even when the body moves.

With the biological information detection apparatus of Embodiment 1, it is possible to always monitor heart rate and blood pressure without disturbing the subject's motion, even during sleep. This allows for construction of a system which always monitors a patient in hospital and issues an alert to medical staff in the event of abnormality, for example. It is also possible to monitor the heart rate of a patient with sleep apnea syndrome during the night at home. Moreover, it is possible to perform stress sensing easily as described above in daily life for more fulfilling life.

(Embodiment 2)

As Embodiment 2, a description is given of a system which measures blood oxygen saturation in a non-contact manner. The major role of blood is to receive oxygen from lungs, deliver the received oxygen to tissues, receive carbon dioxide from tissues, and thereby circulate the received carbon dioxide to the lungs. 100 ml of blood contains about 15 g of hemoglobin. Hemoglobin which binds to oxygen is called oxyhemoglobin ($HbO_2$), and hemoglobin which does not bind to oxygen is called deoxyhemoglobin (Hb). As illustrated in FIG. 3, oxyhemoglobin and deoxyhemoglobin have different absorption characteristics. In a system according to an aspect of the present disclosure, the ratio of these two types of hemoglobin (that is, oxygen saturation) is calculated from reflected light in the infrared wavelength range and reflected light in the green wavelength range. The oxygen saturation refers to a value indicating how much hemoglobin in blood binds to oxygen. The oxygen saturation is defined by the following formula:

$$\text{Oxygen Saturation} = C(HbO_2)/[C(HbO_2)+C(Hb)] \times 100 \, (\%)$$

Herein, C(Hb) is the concentration of deoxyhemoglobin, and $C(HbO_2)$ is the concentration of oxyhemoglobin.

The living body includes components that absorb light in the visible to near-infrared wavelength range in addition to blood. However, the absorptivity changes with time mainly due to hemoglobin in arterial blood. Accordingly, the blood oxygen saturation in arterial blood can be measured with a high level of accuracy based on changes in absorptivity. Arterial blood pumped from the heart moves in vessels as pulse waves while venous blood does not include pulse waves. Light projected onto the living body is absorbed in each layer of the living body, such as arteries, veins, and tissues other than blood while transmitted through the living body. The tissues other than arteries do not change in thickness with time. The intensity of the internal scattered light from the living body changes with time as the thickness of arterial layers changes due to pulsation. The changes in intensity of the internal scattered light reflect changes in thickness of arterial layers and include no influence of venous blood and the other tissues. Accordingly, by focusing on only changes in the internal scattered light, information on arterial blood can be obtained. The pulse rate is also obtained by measuring the period of the component changing with time.

As Embodiment 2, a description is given of an example of measurement of biological information using one camera. In Embodiment 1, two cameras are used to acquire signals of different light source wavelengths. This method has an advantage that existing cameras are available. However, the two cameras need to be configured to capture images in conjunction with each other, thus complicating the system configuration. Moreover, the two cameras provide two sets of video data independent of each other, and synchronized processing for the sets of video data is complicated. An aspect of the present disclosure implements a biological information detection apparatus capable of simultaneously acquiring data of images of light with two wavelengths using one camera.

Figure 7A:
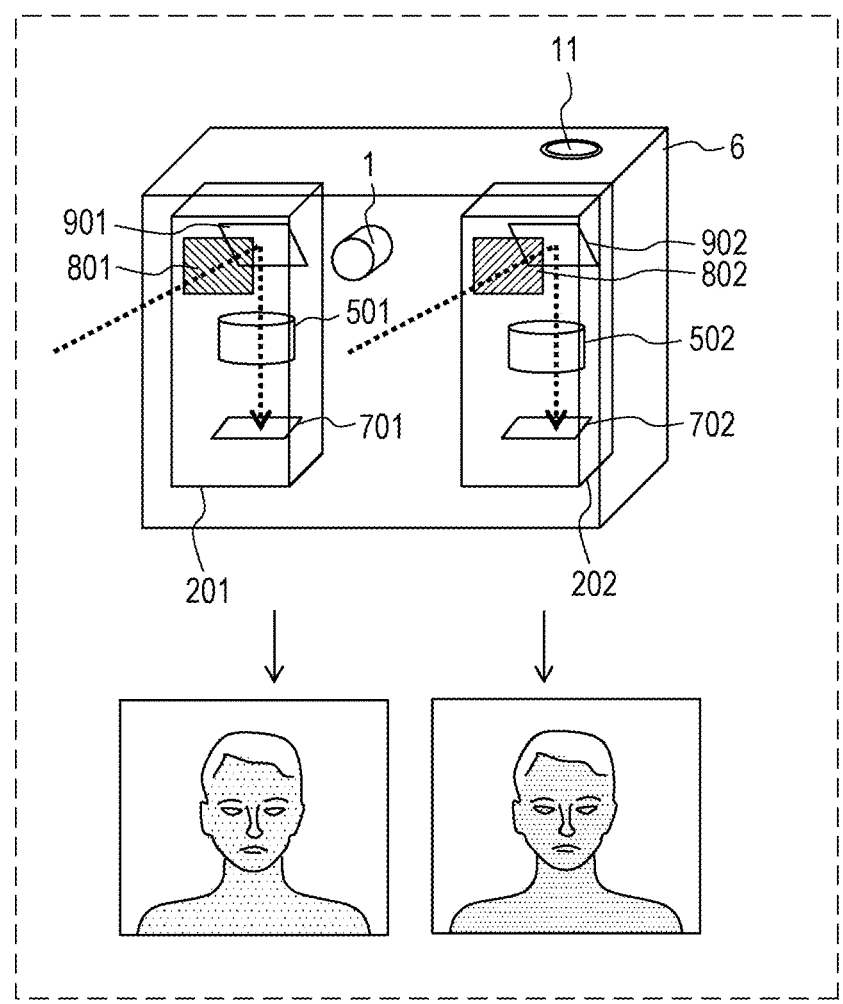
FIG. 7A is a diagram illustrating an example of the configuration of a biological information detection apparatus of Embodiment 2.
Figure 7B:
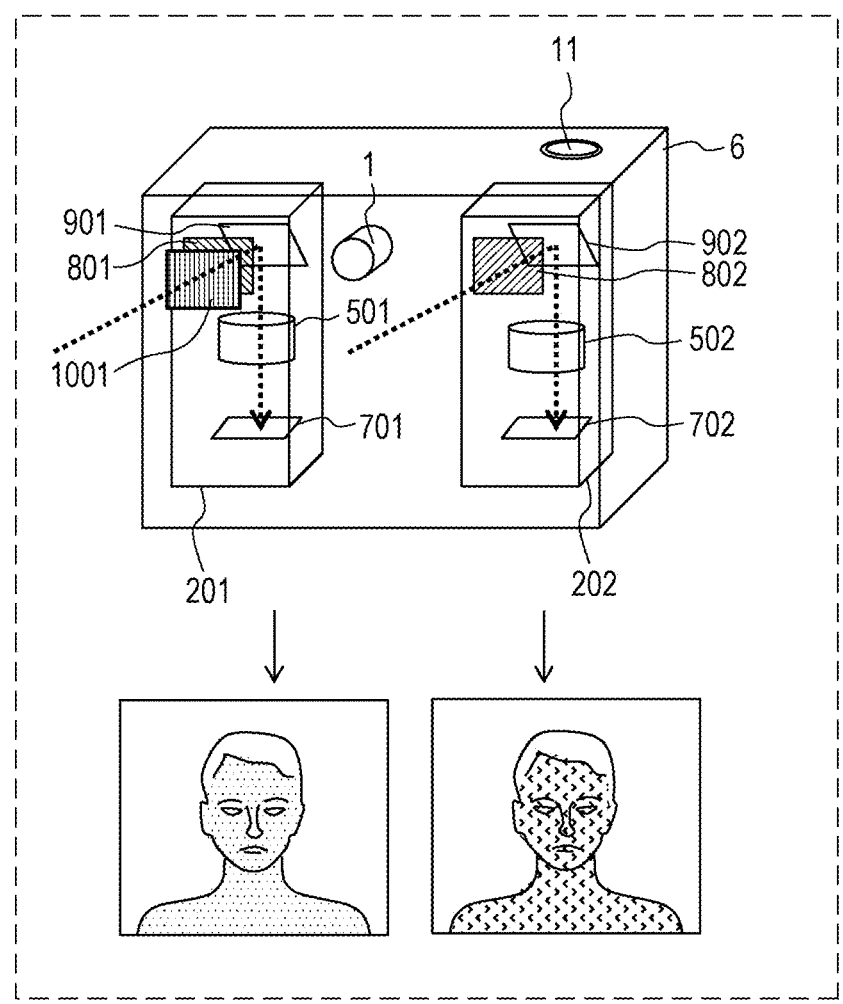
FIG. 7B is a diagram illustrating an example of the configuration of a biological information detection apparatus of Embodiment 2.

In Embodiment 2, a description is given of an example of measurement of blood oxygen saturation. FIG. 7A is a diagram illustrating the configuration of the biological information detection apparatus of Embodiment 2. The biological information detection apparatus includes a dual lens stereo camera structure including cameras 201 and 202 as two imaging systems. In the specification, this method is referred to as a stereo camera method. In the biological information detection apparatus, reflected light from a living body irradiated with a light source 1, which projects a pattern of near-infrared light with a wavelength of 830 nm, are transmitted through band-pass filters 801 and 802. The travel direction of the reflected rays is bent at 90 degrees by mirrors 901 and 902, so that images are formed on imaging surfaces of image sensors 701 and 702 through lenses 501 and 502, respectively. The band-pass filters 801 and 802 are band-pass filters that transmit only near-infrared light with wavelengths of 830±15 nm and transmit only green light with wavelengths of 520 to 600 nm, respectively. The image sensor 701, which receives near-infrared light, can be a near-infrared image sensor, and the image sensor 702, which receives visible light, can be a normal monochrome image sensor, a near-infrared image sensor, or a normal color image sensor. When the image sensor 702 is a visible color image sensor, the band-pass filter 802 is designed to have properties of transmitting only visible light with wavelengths of 400 to 650 nm. Moreover, as illustrated in FIG. 7B, a linear polarization filter 1001 may be provided on an optical path to the near-infrared imaging camera. Embodiment 2 employs the light source 1, which is a laser light source projecting a pattern of near-infrared light with a wavelength of 830 nm. Laser light has linear polarization properties, and the surface reflected light which is reflected on the skin surface retains the linear polarization properties of the light source. On the other hand, the internal scattered light which enters the skin, repeatedly scatters, and exits from the skin loses the linear polarization properties. As already described, information within the living body (blood flow information, for example) is included in the internal scattered light. By placing the linear polarization filter 1001 perpendicularly to the direction of polarization of the laser light source (that is, in the cross Nicole state), the surface reflected light from the skin surface is prevented from reaching the near-infrared image sensor 701, so that the internal scattered light is acquired efficiently. However, use of such a polarization filter reduces the amount of signals that can be acquired. It is therefore preferable that whether to use a linear polarization filter is properly determined in accordance with the measurement conditions and system specifications. When the light source produces a lot of light leakage to an area other than the regions in which light from the light source projecting a dot array pattern is projected in the form of dots (that is, the area onto which light should not be really projected), use of a polarization filter can significantly increase the signal-to-noise ratio of biological information.

When a shutter button 11 is pressed, the image sensors 701 and 702 acquire video images of the living body.

In a similar manner to Embodiment 1, the calculator 22 of the computer 20 first detects the human body from the near-infrared video image and extracts a particular portion (a forehead portion, for example) of the face surface. From the near-infrared video image outputted from the image sensor 701, the surface reflected light component and internal scattered light component are separately measured and are subjected to an operation to provide a signal representing heartbeat information. From the green video image outputted from the image sensor 702, a signal representing heartbeat information is also acquired.

Figure 8:
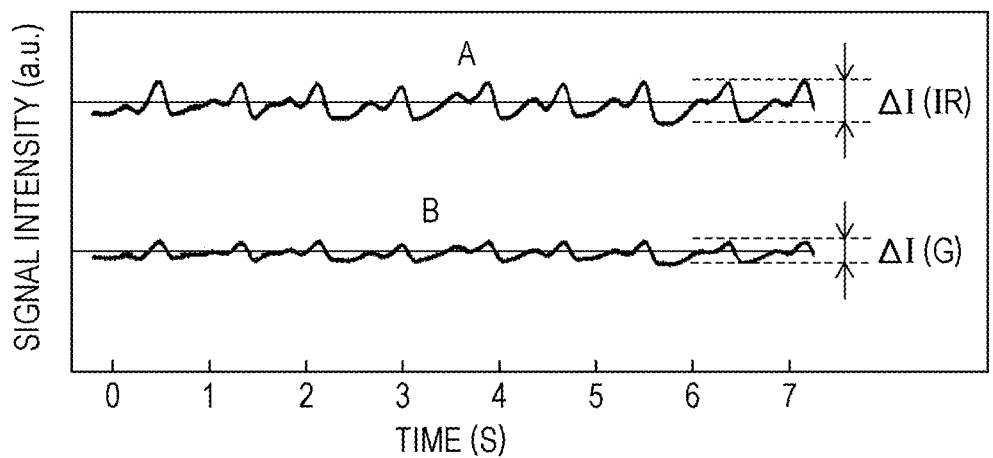
FIG. 8 is a diagram illustrating an example of time changes in internal scattered light intensity in Embodiment 2.

FIG. 8 is a diagram illustrating an example of changes in intensity of the acquired signals with time. The intensity of signal A obtained from the near-infrared video image and the intensity of signal B obtained from the green video image both fluctuate with time. Blood oxygen saturation $SpO_2$ is calculated by the following formula:

$$SpO_2 = a + b \times (\log(\Delta l(G)/li(G))/(\log(\Delta l(IR)/li(IR)))$$

Herein, li(IR) and li(G) are intensities of near-infrared light and green light on the living body surface, respectively. Δl(IR) and Δl(G) are time averages of the fluctuation components of the internal scattered light, in the near-infrared wavelength range and green wavelength range, respectively. a and b in the above formula can be determined based on the relation with values measured by an existing pulse oximeter.

To confirm the accuracy of the biological information detection apparatus, the system of Embodiment 2 is used to measure the oxygen saturation at a fingertip. The oxygen saturation is measured at the fingertip with the blood flow stopped by using a belt, which is used in blood pressure measurement, to apply pressure to the upper arm to a constant pressure (200 mmHg).

A commercially available finger pulse oximeter is attached to the forefinger. The oxygen saturation at the middle finger is measured in a non-contact manner by the system of Embodiment 2. After the aforementioned a and b are determined by the first measurement, the blood oxygen saturation $SpO_2$ is measured.

Figure 9:
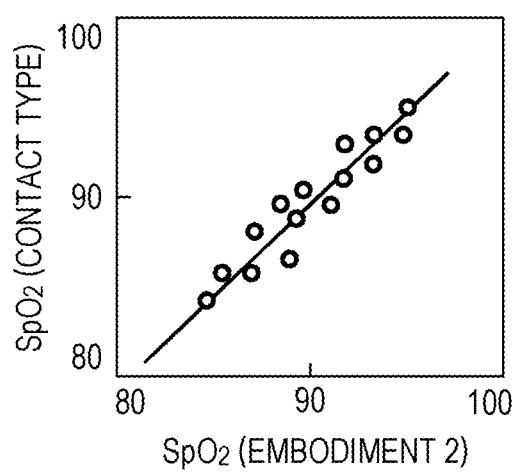
FIG. 9 is a diagram illustrating results from measuring blood oxygen saturation using the method of Embodiment 2 and a conventional method.

FIG. 9 illustrates results of comparison between measured values obtained by the pulse oximeter (indicated by the vertical axis) and measured values in the embodiment (indicated by the horizontal axis). These results substantially correspond to each other. This shows that the system of Embodiment 2 measures the oxygen saturation with a high level of accuracy. With the method of Embodiment 2, the pulse rate can be simultaneously measured from pulse waves illustrated in FIG. 8 together with the blood oxygen saturation.

According to Embodiment 2, the imaging system is composed of a single stereo camera. This makes the entire system compact and simplifies the configuration for signal processing, from image signal processing to oxygen saturation calculation, thus implementing both easy operation and high-speed processing.

(Embodiment 3)

As Embodiment 3, a description is given of another method of measuring blood oxygen saturation using one camera. Embodiment 2 includes a stereo camera configuration in which one camera includes two optical systems and two image sensors. Embodiment 3 employs a system which acquires two different images corresponding to two wavelengths with one image sensor by using plural lenses to separate images. The method of Embodiment 3 is referred to as a stereo lens method. The system of the stereo lens method is described with reference to FIG. 10.

Figure 10:
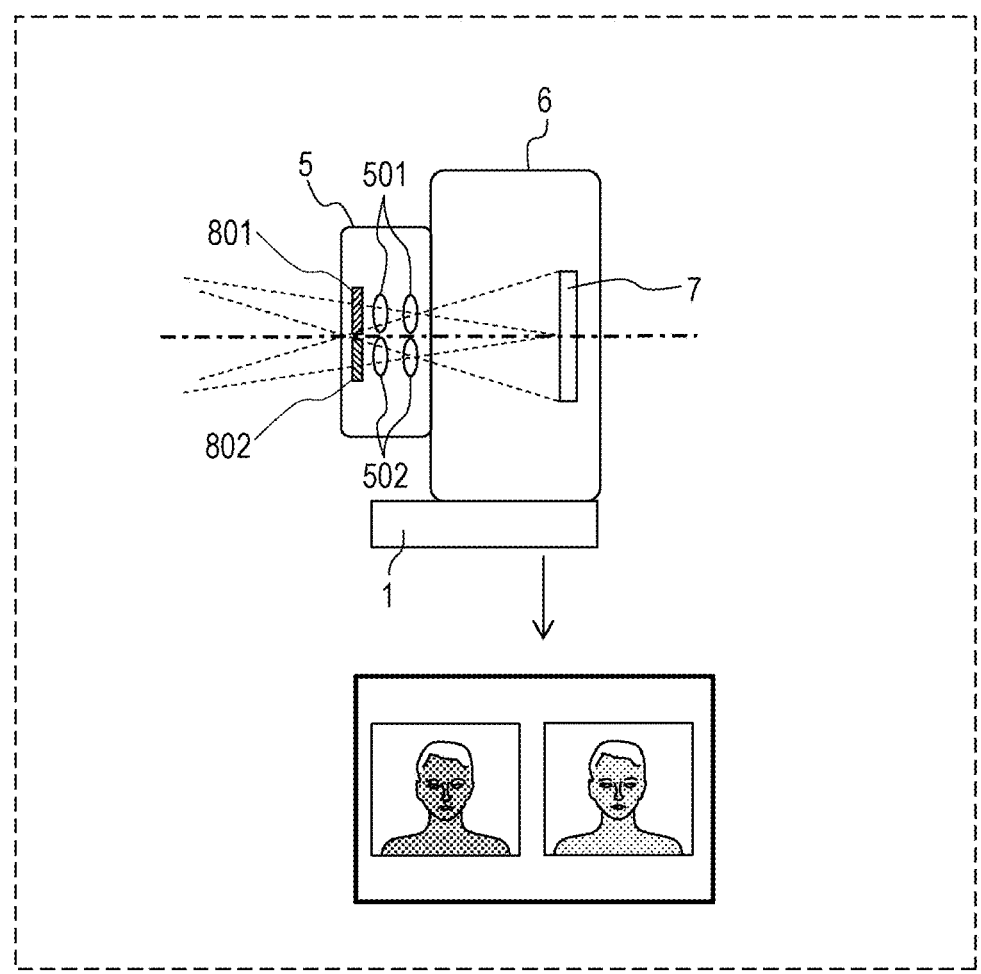
FIG. 10 is a diagram illustrating the configuration of a biological information detection apparatus of Embodiment 3.

FIG. 10 is a cross-sectional view schematically illustrating a part of a biological information detection apparatus of Embodiment 3. The biological information detection apparatus includes a light source 1 that projects a pattern of near-infrared light with a wavelength of 850 nm and two pairs 501 and 502 of lenses within a lens 5. The pairs 501 and 502 of lenses are designed to form images in different regions of the imaging surface of one image sensor 7. In front of the lenses 501 and 502, two band-pass filters 801 and 802 are arranged, respectively. The band-pass filters 801 and 802 transmit light with a wavelength of 850 nm and transmit light with wavelengths of 520 to 600 nm, respectively.

With the aforementioned configuration, two images of light having two wavelengths captured at the same time are acquired using the one image sensor 7. The image sensor 7 is a near-infrared image sensor illustrated in FIG. 4B. The controller 26 calculates biological information from the two images in a similar manner to Embodiments 1 to 3. According to Embodiment 3, one image signal includes information of two images corresponding to two different wavelengths captured at the same time, thus facilitating the operation processing.

A description is given of the result of stress sensing using a system of the stereo lens method. There is a conventional method which detects a decrease in temperature of the nose portion due to stress or concentration using thermography. The blood flow at the nose portion is reduced due to psychological changes, causing a decrease in temperature at the nose portion. The method of detecting a decrease in temperature with thermography is performed in general. The temperature in the face surface changes due to changes in blood flow. If such a change in blood flow is measured with a high level of accuracy, stress sensing can be performed with a higher level of accuracy and with higher response than stress sensing by measuring changes in surface temperature resulting from changes in blood flow.

Figure 11A:
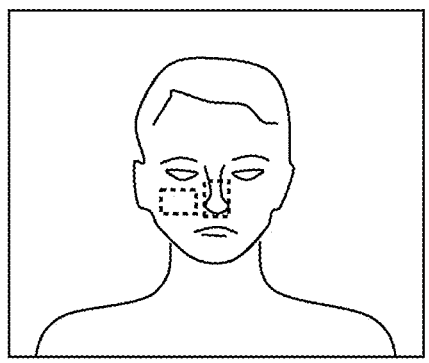
FIG. 11A is a diagram illustrating a nose portion and a cheek portion in an image acquired in Embodiment 3.
Figure 11B:
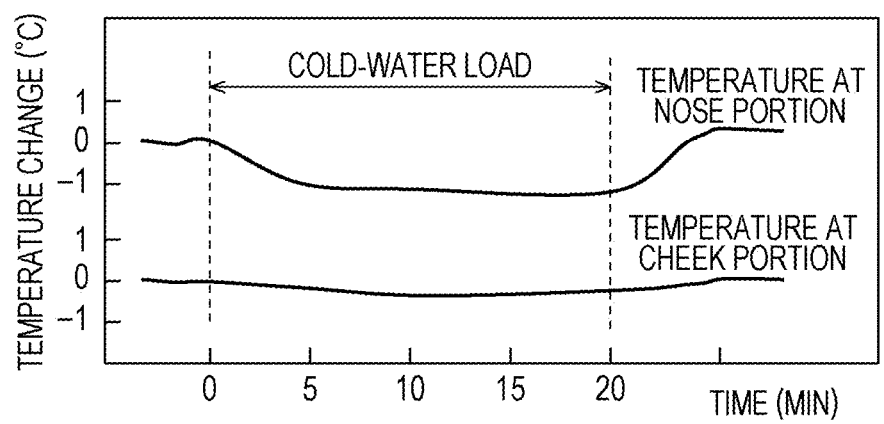
FIG. 11B is a diagram illustrating results from stress sensing using thermography.

Stress sensing is performed with a conventional method using thermography and with a method using the biological information detection apparatus according to an aspect of the present disclosure for comparison. Herein, stress is given by cold-water loading, in which the subject's right hand is immersed in cold water. At a nose portion and a cheek portion surrounded by dot lines in FIG. 11A, blood information is measured using image signals obtained by the biological information detection apparatus according to an aspect of the present disclosure, and changes in temperature are measured using thermography. FIG. 11B is a diagram illustrating the result from conventional stress sensing using thermography. After the cold-water loading is started, the temperature at the nose portion gradually decreases about 1.2° C. over about three minutes and is stabilized. After the cold-water loading is terminated, the temperature at the nose portion also spends about three minutes to return. On the other hand, the diagram shows that the temperature at the cheek portion is not influenced by the cold-water loading and remains stable.

Figure 11C:
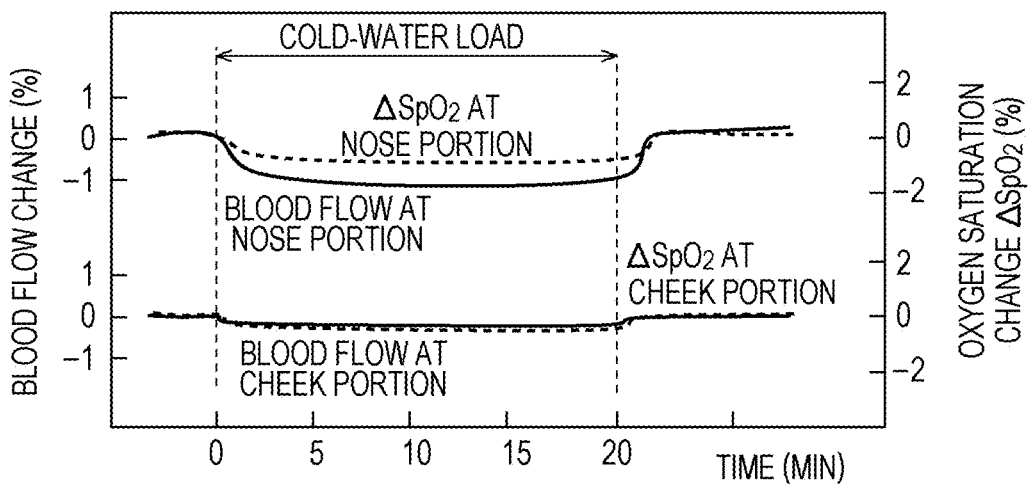
FIG. 11C is a diagram illustrating changes in blood flow and blood oxygen saturation obtained using the biological information detection apparatus of Embodiment 3.

FIG. 11C is a diagram illustrating changes in the blood flow and blood oxygen saturation obtained using the biological information detection apparatus of Embodiment 3, which employs the stereo lens method. Data in the regions corresponding to the nose and cheek portions (indicated by the dot lines in FIG. 11A) is extracted from data of the blood flow and oxygen saturation ($SpO_2$) in the face part. In FIG. 11C, the solid line indicates changes in blood flow with time, and the dot line indicates changes in oxygen saturation ($\Delta SpO_2$) with time. As illustrated in FIG. 11C, the blood flow at the nose portion is on a decreasing trend immediately after the cold-temperature stimulus is applied, showing quick response. On the other hand, the blood flow at the cheek portion remains virtually unchanged. As for the oxygen saturation, it is observed that the oxygen saturation decreases at the nose portion with the decreasing blood flow while not changing at the cheek portion.

As apparent from the results, many data can be obtained by measuring blood flow and oxygen saturation at different sites of the face. Based on these data, it is possible to detect the emotion, physical conditions, or concentration with a high level of accuracy. Changes in blood flow due to the influence of the autonomic nervous system vary from site to site in the face. It is therefore particularly important to measure changes in blood flow at a particular site using a camera. In this process, the measurement accuracy can be improved by simultaneously performing measurement for the site where the blood flow changes little as a reference.

In this configuration, the biological information detection apparatus includes only one image sensor, and it is impossible to separately use image sensors for near-infrared light and visible light. In the aforementioned example, the image sensor 7 is a near-infrared image sensor but may be a color image sensor. As illustrated in FIG. 4C, the red, green, and blue pixels of a color image sensor are also sensitive to near-infrared light with wavelengths of not less than 800 nm. Accordingly, the band-pass filter 801 is configured to transmit light with a wavelength of 850 nm corresponding to the wavelength of the light source 1, and the band-pass filter 802 is configured to transmit visible light with wavelengths of 400 to 650 nm. In a region of the image sensor where light transmitted through the band-pass filter 801 forms an image, a near-infrared image is acquired. In a region of the image sensor where light transmitted through the band-pass filter 802 forms an image, a three-color image of red, green, and blue is acquired. In the region of the image sensor for near-infrared images, the sensitivity to near-infrared light is varied due to slight differences in near-infrared transmission properties between the red, green, and blue color filters in practice.

In such a case, it is preferable that the differences in sensitivity between the color filters are acquired in advance for sensitivity correction, for example. Using the color image sensor allows for body motion correction with a high level of accuracy as described above.

(Embodiment 4)

As Embodiment 4, a description is given of an example using a combination of human body detection and biological information sensing. A system according to an aspect of the present disclosure is able to rapidly detect a human body in an image and implement quick and highly accurate measurement of biological information, such as heartbeat, based on data of the region corresponding to the detected human body. This can implement a monitoring system in a personal space, such as a bathroom, a toilet, or a bedroom. In such personal spaces, it is particularly important to respect privacy. In a system which always takes images of the target with a high-resolution camera and uses the taken images, there is a concern about invasion of privacy by potential leakage of the images and psychological burden due to the existence of the camera.

As the population ages, it is said that 10000 to 20000 people per annum are dead while bathing, which is far greater than the annual number of traffic fatalities of 4000 to 5000. Deaths in bathrooms are caused by both accidents and diseases. A high proportion of fatalities are elderly persons, and most of the deaths occur in winter. As the population ages, the annual number of fatalities in bathrooms increases. As for such deaths in bathroom, regardless of whether the deaths are caused by illness or accident, there are many cases where fatalities could have been avoided by early discovery of abnormalities. Since the bathrooms are closed private spaces, abnormalities are discovered too late, resulting in death in many cases. There is a strong demand for a system capable of monitoring the target in a bathroom while respecting personal privacy.

Figure 12:
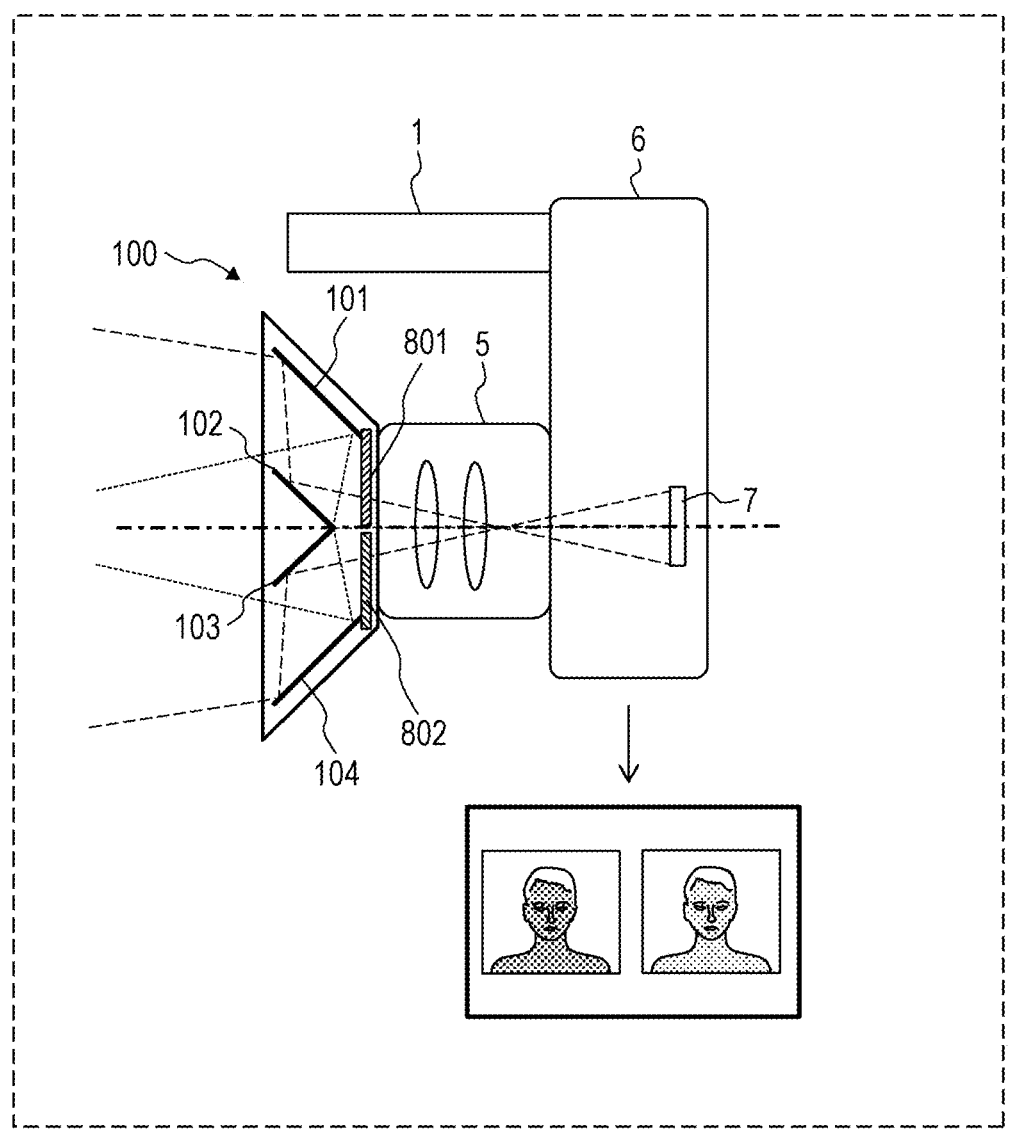
FIG. 12 is a diagram illustrating the configuration of a biological information detection apparatus of Embodiment 4.

A camera system of Embodiment 4 employs a method different from Embodiment 3 measuring biological information using one camera. FIG. 12 is a cross-sectional view schematically illustrating the configuration of the biological information detection apparatus in Embodiment 4. This apparatus includes a stereo adaptor 100, which is attachable to a normal camera lens. The stereo adaptor 100 is an attachment including four reflection mirrors 101, 102, 103, and 104 and two band-pass filters 801 and 802. By using the stereo adaptor 100, two images corresponding to two wavelengths can be separately formed in two different regions of the imaging surface of an image sensor 7. This method is referred to as a stereo adaptor method.

With the stereo adaptor method, by using two pairs of reflection mirrors facing each other, two different images corresponding to two wavelengths can be acquired through the one image sensor 7. The image of the target illuminated with a pattern of near-infrared light having a wavelength of 830 nm is acquired by a camera in which the stereo adaptor 100 is attached to the tip of the lens 5. The optical paths are bent twice by a pair of the reflection mirrors 101 and 102 and a pair of the reflection mirror 103 and 104 to be introduced to a lens 5. Between the lens 5 and the reflection mirrors 101 and 102 and between the lens 5 and the reflection mirrors 103 and 104, band-pass filters 801 and 802 are provided, respectively. The band-pass filters 801 and 802 transmit light with a wavelength of 830 nm and transmit light with wavelengths of 520 to 600 nm, respectively.

The biological information detection apparatus acquires images corresponding to two wavelengths acquired at the same time with the one image sensor 7. The image sensor 7 is composed of the near-infrared image sensor illustrated in FIG. 4B. The basic idea is the same as Embodiment 3. The stereo lens method has an advantage that the lens size can be reduced and the entire system size can be thereby reduced. On the other hand, the stereo adaptor method increases the entire system size. However, the stereo adaptor method has advantages that the system can employ high-performance camera lenses to improve the resolution and employ lenses having different magnifications or zoom lenses. The high flexibility of the system as described above is one of the advantages of the stereo adaptor method. Moreover, the system of the stereo lens method cannot take in sufficient light because of the small numerical aperture of the lenses and has low sensitivity. On the other hand, the stereo adaptor method can employ a lens with a large numerical aperture, and allows for construction of a high-sensitivity system. The system of the stereo adaptor method is able to perform sensing under darker conditions.

In Embodiment 4, in a similar manner to Embodiment 3, the image sensor 7 can be a color image sensor. In this case, the band-pass filter 802 needs to be a band-pass filter transmitting visible light with wavelengths of 400 to 650 nm.

Figure 13B:
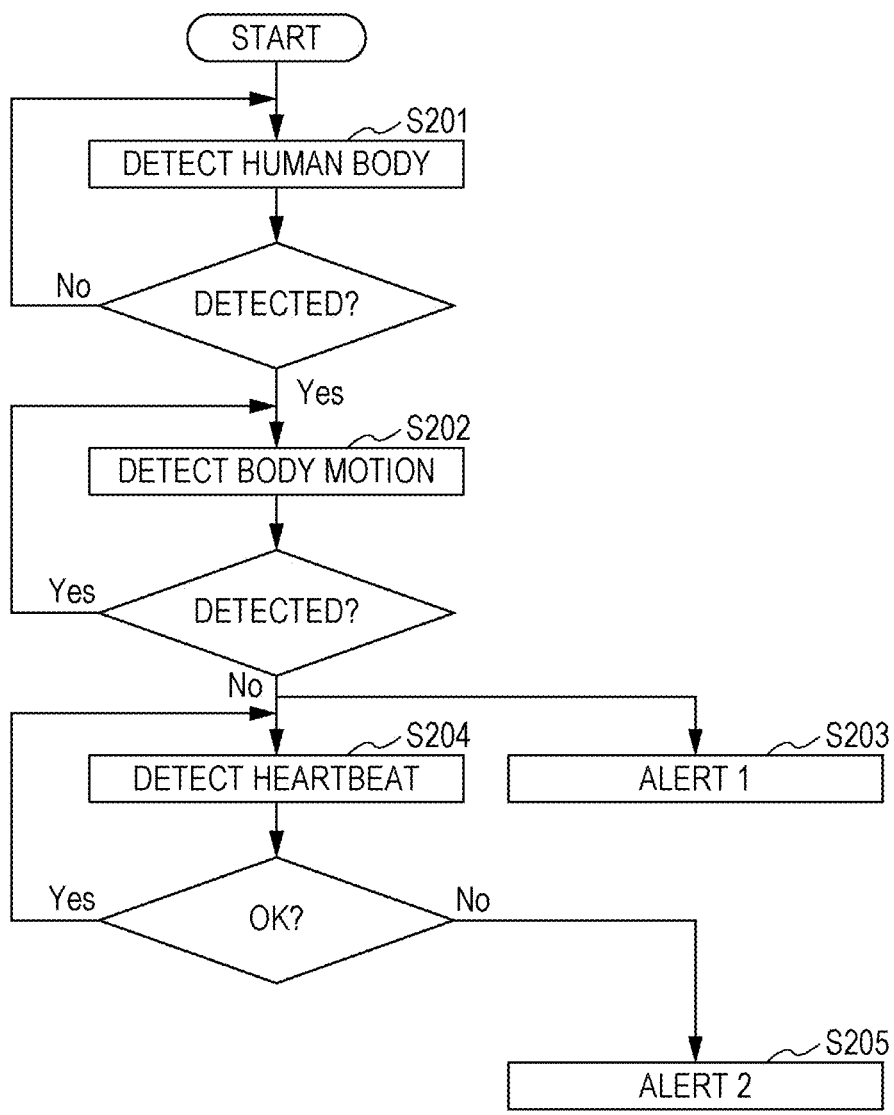
FIG. 13B is a diagram illustrating the algorithm of the monitoring system using the biological information detection apparatus of Embodiment 4.

A description is given of an actual monitoring algorithm of Embodiment 4 using FIGS. 13A and 13B. The biological information detection apparatus illustrated in FIG. 12 is installed at a corner of the bathroom and is configured to monitor the entire bathroom as illustrated in part (a) of FIG. 13A. Based on the taken near-infrared image, human body detection (part (b) of FIG. 13A), body motion detection (part (c) of FIG. 13A), and abnormal heart rate detection (part (d) of FIG. 13A) are performed. When no body motion is detected after the human body is detected, a first alert (alert 1) is issued to the bathing person to call for attention, for example. When any heartbeat abnormality is then detected, a second alert (alert 2) is issued to a person outside of the bathroom, for example. Hereinafter, the operation of the monitoring system of Embodiment 4 is described in more detail with reference to the flowchart of FIG. 13B.

FIG. 13B is a flowchart illustrating the operation of the monitoring system of Embodiment 4. First, the calculator 22 detects a human body by the same method as Embodiment 1 based on data of the acquired near-infrared image (step S201). When the human body is detected, the calculator 22 goes to subsequent body motion detection in step S202. In this process, the data of the image used for human body detection is not recorded in a storage device and is replaced with image data of the next video frame other than data of the human body region. In such a manner, the watching system does not leave personally identifiable image data, so that the privacy is protected.

Next, the calculator 23 compares data of plural successive frames in terms of the detected human body region to detect body motion (step S202). When no body motion is detected for a certain period of time (30 seconds, for example) or more, for example, alert 1 is issued to the bathing person (step S203). This can be an alert such as "Are you awake? It's dangerous to sleep in the bathroom. Please press OK button". Alert 1 is intended to warn the bathing person and confirm the person's conditions. When any body motion is not detected, the calculator 23 measures pulsation (step S204). When the measured pulsation is small or any pulsation is not detected, alert 2 is issued (step S205). This is an alert for people outside of the bathroom (families, caretakers, ambulance workers, and the like). The alert 2 can be an alert intended to ask people previously set in the system for confirmation and help, by voice alert, telephone, or the Internet.

According to Embodiment 4, the simple monitoring system executes three detection steps, including (1) human body detection, (2) body motion detection, and (3) heartbeat measurement, thus implementing highly reliable monitoring.

In the above example, (1) human body detection, (2) body motion detection, and (3) heartbeat measurement are executed step by step. However, after human body detection, body motion detection and heartbeat measurement may be performed in parallel. With such a configuration, the monitoring system can constantly monitor the heartbeat of the bathing person and give a proper advice to the person. There have been many drowning fatalities due to changes in heartbeat associated with vasoconstriction resulting from a difference in temperature between an undressing room and a bathroom, reduction in brain and heart blood flows associated with an increase in blood flow in the body surface, and lightheadedness (dizzy feeling) resulting from orthostatic hypotension associated with the reduction in brain and heart blood flows. Such accidents can be prevented by measuring changes in physical conditions of the bathing person with a heartbeat monitor in real time and giving a feedback to the bathing person. If the heart rate increases significantly, for example, the monitor system can issue a message such as "Be careful about lightheadedness. Hold the handrail and move slowly when standing".

For monitoring systems in private spaces, such as bathrooms, toilets, and bedrooms, privacy protection is particularly important. In the monitoring system of Embodiment 4, the taken images are used in image signal processing only for human body detection and heartbeat measurement. The image data itself is not recorded in a storage medium and is always replaced with data of the next frame after human body detection. Moreover, the monitoring system is designed not to include a mechanism for outputting image data. Accordingly, the image data in the monitoring system cannot be acquired from the outside. The monitoring system is thus configured to prevent the privacy from being invaded by an attack from a hacker having a malicious intention or the like. For monitoring systems in private spaces, it is particularly important to secure the privacy psychologically with a hardware mechanism. The monitoring system of Embodiment 4 allows for privacy-conscious monitoring at home.

Furthermore, as for long-period monitoring in bedrooms or hospital rooms, measurement is performed in a bright environment during daytime, including exposure to direct sunlight, and is performed in a dark environment during bedtime at night, where the illumination is reduced. It is difficult for the conventional biological information detection apparatus to execute long-period monitoring while stably detecting biological information when the measurement environment varies significantly as described above. The biological information detection apparatus using near-infrared light and green light according to an aspect of the present disclosure is able to constitute a monitoring system not influenced by environmental variations.

(Embodiment 5)

As Embodiment 5, a description is given of an application example to driver monitoring. Currently, autonomous driving techniques for automobiles are being developed. Other than full autonomous driving not allowing human beings to drive, it is desirable to perform seamless switching between human driving and self-driving. There is a demand especially for a mechanism which always monitors the driver's state and perform rapid switching to self-driving when the driver's state is not suitable for driving. Such seamless switching of driving requires a driver monitoring system capable of always checking the driver's state. Moreover, the measurement environment varies significantly also in the case of driver monitoring. The brightness in an automobile varies significantly. The inside of an automobile is bright in the daytime and is sometimes subject to direct sunlight exposure in the morning and evening. At night, it is dark in the automobile, and visible light is hardly detected. Moreover, the target in the automobile vibrates with respect to the camera because of vibration of the automobile. Moreover, there is an influence of body motion due to driving operation. The environment of driver monitoring is very severe as the environment for biological information detection. As already described, the method of the biological information detection apparatus according to an aspect of the present disclosure is resistant to variation in illumination environment and is capable of eliminating the influence of body motion. The biological information detection apparatus of the present disclosure is therefore suitable for driver monitoring.

As the camera system of Embodiment 5, the stereo adaptor method illustrated in FIG. 12 described in Embodiment 4 is employed. The near-infrared pattern is a pattern of light with a wavelength of 940 nm, which is absorbed by moisture and occupies a small proportion of sunlight. The band-pass filters 801 and 802 are therefore band-pass filters which transmit light with a wavelength of 940 nm and wavelengths of 520 to 600 nm, respectively.

Figure 14:
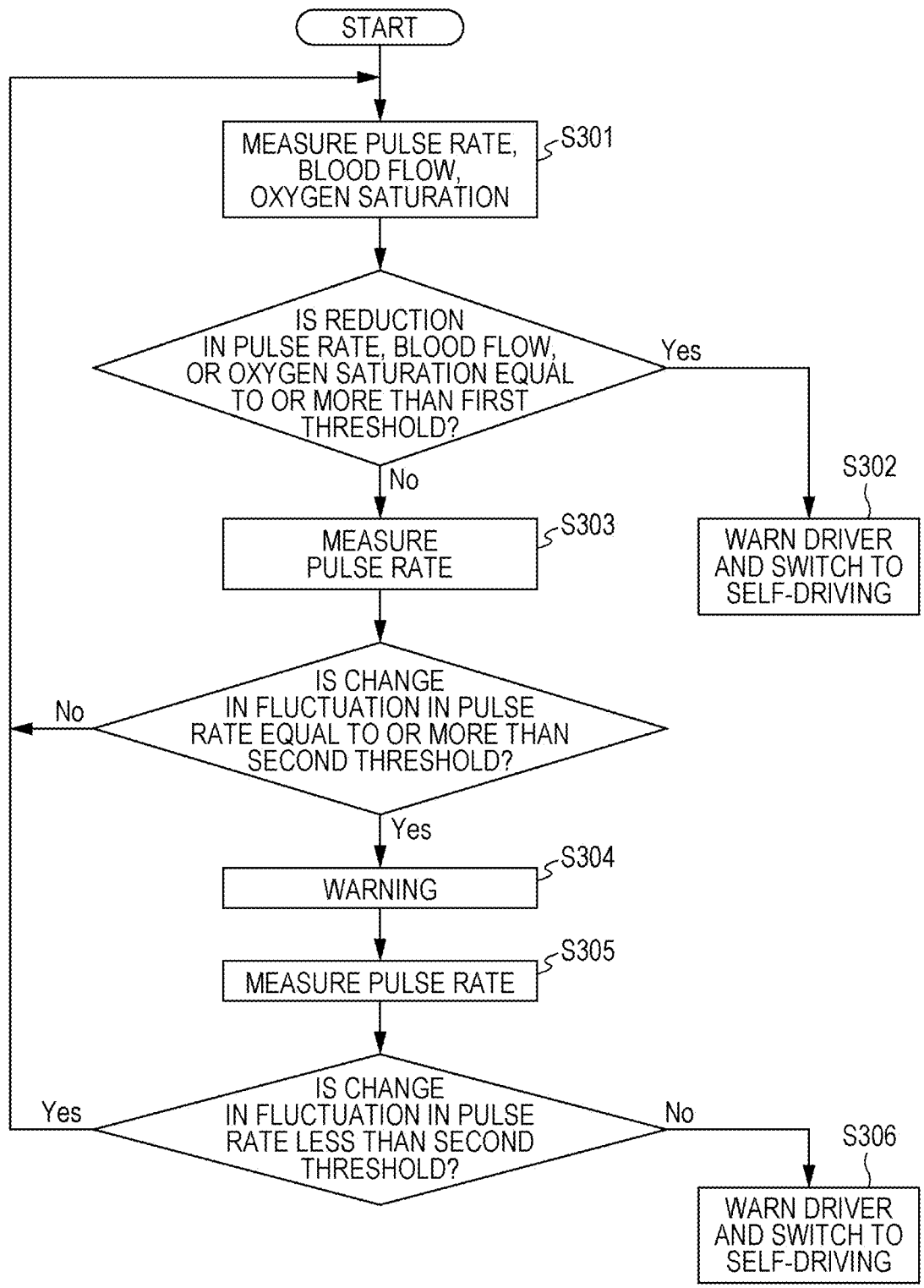
FIG. 14 is a diagram illustrating a flow of driver monitoring in Embodiment 5.

Driver monitoring is performed using the biological information detection apparatus illustrated in FIG. 12. The biological information detection apparatus measures pulse rate, blood flow, and oxygen saturation from the near-infrared image and green image. Herein, the blood flow is calculated from the magnitude of pulsation, that is, the amplitude of pulse wave signals. Stress, concentration, and sleepiness can be determined from the fluctuations in pulse with time. The flow chart of driver monitoring is illustrated in FIG. 14.

The biological information detection apparatus is used to measure the pulse rate, blood flow, and oxygen saturation (step S301). When based on the measurements, it is detected that the pulse rate, blood flow, or oxygen saturation decreases rapidly by a first threshold or more, the monitoring system determines that the driver's physical conditions have changed and forcibly performs switching to self-driving after warning (step S302). Herein, gradual reduction in pulse rate and an increase in fluctuations in pulse rate are considered to indicate that the driver loses concentration or is sleepy. The pulse rate is measured again (step S303). When detecting that the fluctuations in pulse rate change by a second threshold or more, the driver monitoring system warns the driver (step S304). The pulse rate is measured again (step S305). When the changes in fluctuations in pulse rate are not reduced to the second threshold, the driver monitoring system forcibly performs switching to self-driving after warning (step S306). Such a driver monitoring system is applicable to normal car driving as well as autonomous driving. Driving safety can be improved by only warning the driver when the driver's physical conditions are changing or the driver's concentration is lowered.

(Embodiment 6)

As Embodiment 6, a description is given of a method of measuring blood oxygen saturation using one camera without dividing an image by an optical system. The methods described in Embodiments 3 to 5 split light having two wavelengths for sensing and calculates the biological information such as oxygen saturation. A biological information detection apparatus of Embodiment 6 acquires two image signals of light with different wavelengths by an image sensor without dividing an image.

Figure 15A:
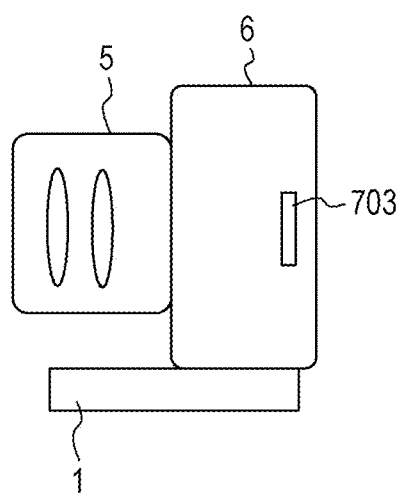
FIG. 15A is a diagram schematically illustrating the configuration of a biological information detection apparatus of Embodiment 6.

FIG. 15A is a diagram schematically illustrating the configuration of the biological information detection apparatus of Embodiment 6. The biological information detection apparatus separates two images corresponding to two wavelengths with an image sensor 703, not with an optical system. The near-infrared light and green light from a subject illuminated with a pattern of near-infrared light with a wavelength of 860 nm forms an image on the imaging surface of the image sensor 703 through a lens 5. The image sensor 703 used herein, different from a normal image sensor, includes color filters G as a band-pass filter transmitting green light and color filters IR as a band-pass filter transmitting near-infrared light.

Figure 15B:
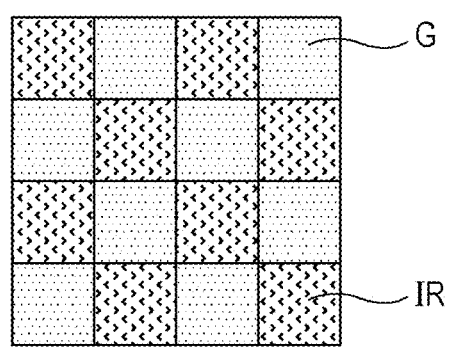
FIG. 15B is a diagram illustrating plural color filters in Embodiment 6.
Figure 15C:
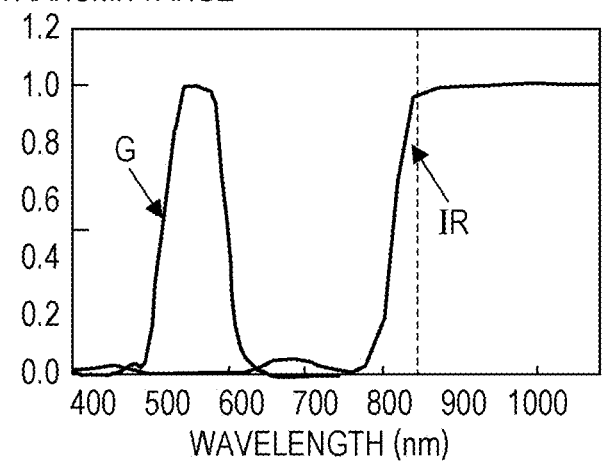
FIG. 15C is a diagram illustrating wavelength dependence of the transmittance of color filters in Embodiment 6.
Figure 15D:
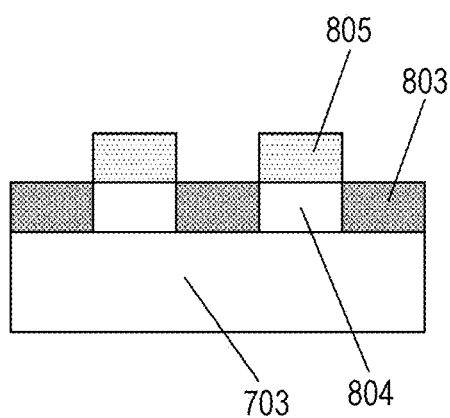
FIG. 15D is a cross-sectional structure view of an image sensor in Embodiment 6.

FIG. 15B is a diagram illustrating plural color films facing plural optical detector cells arrayed on the imaging surface of the image sensor 703. The image sensor 703 includes color filters G selectively transmitting light with wavelengths of 520 to 600 nm and color filters IR selectively transmitting light with wavelengths of not less than 800 nm. The color filters G and IR are arrayed in a checkered pattern. FIG. 15C is a diagram illustrating an example of wavelength-dependence of the transmittances of the color filters G and IR. The image sensor 703 detects two images by green light and 860 nm near-infrared light through the plural photodetector cells (also referred to as pixels). Herein, if the image sensor 703 employs color filters that selectively transmit light with wavelengths of 520 to 600 nm, the image sensor 703 is designed to have a simple configuration. However, green color filters normally used in image sensors are characterized by transmitting infrared light. Accordingly, just using green color filters cannot provide a green image in the presence of near-infrared light, resulting in an image of a mixture of green light and near-infrared light. One of the solutions thereof is to reduce the near-infrared image signal from the image signal of the mixture of green light and near-infrared light on a pixel-by-pixel basis to calculate a green image. However, it is difficult for this method to perform highly accurate detection because of the low noise-to-signal ratio. In Embodiment 6, as illustrated in FIG. 15D, near-infrared absorption filters 805 are formed on green color filters 804 adjacent to near-infrared color filters 803 to bring green light incident on green pixels. By employing such a structure, only green light is incident on the green pixels illustrated in FIG. 15B.

Figure 16A:
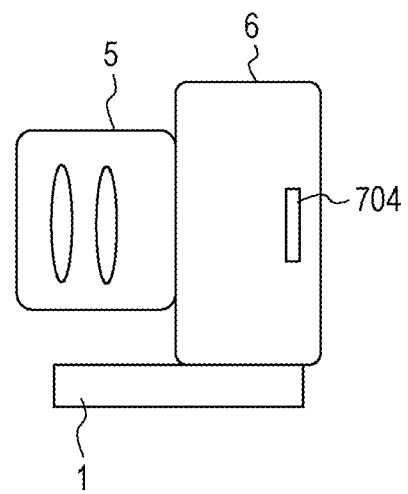
FIG. 16A is a diagram schematically illustrating the configuration of another biological information detection apparatus in Embodiment 6.

FIG. 16A illustrates an example of the biological information detection apparatus using an image sensor 704 having a color filter configuration different from FIG. 15A. Herein, images of visible light and near infrared light are formed on the imaging surface of the image sensor 704 through the lens 5. The image sensor 704 used herein includes photodetector cells to acquire a color image and photodetector cells to acquire a near-infrared image.

Figure 16B:
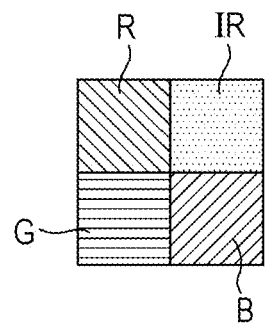
FIG. 16B is a diagram illustrating other plural color filters in Embodiment 6.
Figure 16C:
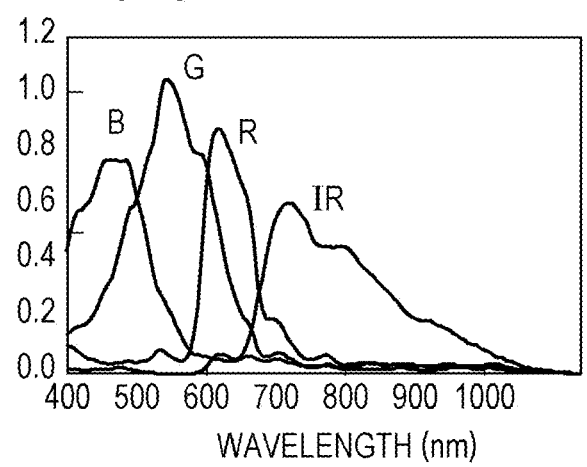
FIG. 16C is a diagram illustrating wavelength dependence of relative sensitivity of an image sensor in Embodiment 6.

FIG. 16B is a diagram illustrating plural color filters arrayed on the imaging surface of the image sensor 704. FIG. 16C illustrates the wavelength dependence of relative sensitivity of pixels facing the respective filters. As illustrated in FIG. 16B, three types of color filters R, G, and B that transmit red, green, and blue light and color filters IR that transmit light with wavelengths not less than 650 nm are arrayed on the imaging surface. Actually, near-infrared absorption filters are formed on the color filters R, G, and B to constitute R, G, and B pixels not receiving near infrared light. In a normal Bayer color filter, two green filters are arranged adjacent to each other in a diagonal direction, and red and blue filters are arranged in the other diagonal direction. In Embodiment 6, one of the two green pixels is replaced with a near-infrared pixel. As illustrated in FIG. 2, red and blue channel signals are not effective to detect biological information. The red and blue pixels are provided herein in order to remove influences of body motion and changes in environmental light from the green signal using the blue and red pixel data. As illustrated in FIGS. 5A to 5C, as for near-infrared light, the surface reflected light component and internal scattered light component are used to remove influences of body motion. In a similar manner, the influences of body motion and changes in environmental light from the green signal can be removed using red or blue signal.

(Other Embodiments)

Hereinabove, the embodiments of the present disclosure are shown by way of example. However, the present disclosure is not limited to the aforementioned embodiments and can be modified variously. The processing described for each embodiment described above is applicable to other embodiments in some cases. Hereinafter, a description is given examples of other embodiments.

In the aforementioned embodiments, the light source projecting a dot array pattern is a laser light source but may be another type of light source. The light source may be a low price LED light source, for example. However, LED light sources have low directionality, and light from LED light sources is likely to spread. It is therefore preferable that a dedicated correction optical system is used or the distance between the imaging object and cameras is limited.

The biological information detection apparatus may include an adjustment mechanism which adjusts the focal point of the optical system. The adjustment mechanism is implemented by a not-illustrated motor and the controller 26 illustrated in FIG. 4D, for example. The adjustment mechanism adjusts the focal point of the optical system so as to maximize the contrast of the image of the dot array pattern projected on the target by the light source. This improves the accuracy in the contrast calculation described in Embodiment 1.

The calculator 22 may be configured to extract the surface reflected light component from the living body surface and based on the surface reflected light component, create information within the epidermis including at least melanin density, presence of spots, and presence of bruises. The surface reflected light component can be obtained by determining whether the contrast exceeds a predetermined threshold in Embodiment 1 or removing the low-frequency component in the image signal, for example.

The present disclosure describes the double camera method using two cameras (FIG. 1A), the stereo camera method in which two pairs of optical systems and two pairs of image sensors are included in a camera (FIGS. 7A and 7B), the stereo lens method using two pairs of lenses and one image sensor (FIG. 10), the stereo adaptor method using one lens adaptor, one lens, and one image sensor (FIG. 12), and the method using an image sensor to separate images (FIGS. 15A and 16A). As already described, each method includes advantages and disadvantages, and it is possible to select an optimal method in accordance with the intended use.

In the present disclosure, the near-infrared pattern light source is a dot array patter but may be another pattern, such as a stripe pattern, a checkered pattern, and a grid pattern, for example.

The present disclosure uses the band-pass filters with wavelengths of 520 to 600 nm for green pixels, but the band-pass filters are not limited to this wavelength range. Light including biological information the most has a wavelength of 570 to 590 nm, and the signal-to-noise ratio is reduced with the distance from the wavelength range of 570 to 590 nm. Accordingly, in the light of only the signal-to-noise ratio, it is possible to use a band-pass filter transmitting light with wavelengths of 570 to 590 nm or use a narrow band light source at a wavelength of 580 nm. However, it is efficient that the environment light is used as green light, and employment of the narrow band-pass filter reduces the sensitivity, thus reducing the measurement accuracy in dark environments. The embodiments of the present disclosure use the band-pass filters with wavelengths of 520 to 600 nm because of the balance between the sensitivity and signal-to-noise ratio. However, the wavelength range can be altered in accordance with the use environment. If the biological information detection apparatus is used in a bright environment, it is desirable to employ a 570-590 nm narrow band filter. On the other hand, if the apparatus is used in a dark environment, the wavelength band is preferably made wider. In light of the signal-to-noise ratio, the wavelength band of the band-pass filter may be limited to a wavelength range of 500 to 620 nm.

As described above, according to the embodiments of the present disclosure, it is possible to measure not only heart rate and blood flow but also blood oxygen saturation in various environments without restricting the subject and without bringing detector devices, such as sensors, into contact with the subject. Based on measurement values of blood flow and oxygen saturation at different sites of the subject, it is also possible to estimate the emotion and physical conditions of the subject.

What is claimed is:

1. A biological information detection apparatus, comprising:
    a light source which projects a pattern of near-infrared light onto an object including a living body;
    an imaging system which includes first photodetector cells detecting light in a near-infrared wavelength range and second photodetector cells detecting light in a visible wavelength range, and is configured to generate a first image signal representing a first image, and a second image signal representing a second image; and
    a calculator, wherein:
    the first image is an image of the object on which the pattern is projected, the image taken in the near-infrared wavelength range,
    the second image is an image of the object taken in the visible wavelength range,
    when brightness of the environmental light is within a low level, the calculator is configured to:
        select the first image signal, and
        calculate biological information based on the first image signal, and
    when the brightness of the environmental light is within a high level, the calculator is configured to:
        select the second image signal, and
        calculate the biological information based on the second image signal.

2. The biological information detection apparatus according to claim 1, wherein the pattern includes a plurality of dots.

3. The biological information detection apparatus according to claim 1, wherein:
    the near-infrared light includes light with wavelengths of not less than 650 nm and not greater than 950 nm, and
    the light in the visible wavelength range includes light with wavelengths of not less than 500 nm and not greater than 620 nm.

4. The biological information detection apparatus according to claim 1, wherein the biological information includes at least one selected from the group consisting of a heartbeat rate of the living body, a blood pressure of the living body, a blood flow of the living body, a blood oxygen saturation level of the living body, a melanin concentration in skin of the living body, information whether or not there is a spot in the skin of the living body, and information whether or not there is a bruise in the skin of the living body.

5. The biological information detection apparatus according to claim 1, wherein the calculator is configured to detect a part of the first image corresponding to the living body in the first image using the first image signal.

6. The biological information detection apparatus according to claim 5, wherein the calculator is configured to determine whether the living body is present at a position corresponding to a pixel included in the first image based on a ratio of a variation of an intensity of the first image signal corresponding to the pixel and an intensity of the first image signal corresponding to each of pixels around the pixel to an average of the intensity of the first image signal corresponding to the pixel and the intensity of the first image signal corresponding to each of the pixels around the pixel.

7. The biological information detection apparatus according to claim 5, wherein the calculator is configured to calculate the biological information based on a ratio of a first intensity average to a second intensity average,
    the first intensity average is an average of intensities of the first image signal corresponding to some pixels selected, in descending order of intensities of the first image signal, from a pixel included in the part of the first image and pixels arranged around the pixel, and
    the second intensity average is an average of intensities of the first image signal corresponding to other pixels selected, in ascending order of intensities of the first image signal, from the pixel and the pixels arranged around the pixel.

8. The biological information detection apparatus according to claim 5, wherein the calculator is configured to calculate the biological information using an average of intensities of the second image signal corresponding to pixels included in a second portion of the second image, the second portion corresponding to the first portion in the first image.

9. The biological information detection apparatus according to claim 1 wherein the calculator is configured to:
   calculate a blood flow of the living body and a blood oxygen saturation level of the living body based on the first and second imaging signals, and
   generate information representing at least one selected from the group consisting of physical condition, emotion, and concentration of the living body based on the blood flow of the living body and the blood oxygen saturation level of the living body.

10. The biological information detection apparatus according to claim 1, wherein
   when the first and second images each include at least one selected from the group consisting of a cheek and a nose of the living body, the calculator is configured to:
   calculate a change in a blood flow with time and a change in a blood oxygen saturation level with time in the at least one selected from the group consisting of the cheek and the nose using the first and second image signals, and
   generate information representing at least one selected from the group consisting of physical condition, emotion, and concentration of the living body using the change in the blood flow with time and the change in the blood oxygen saturation level with time.

11. The biological information detection apparatus according to claim 1, wherein
   when the first and second images each include a cheek and a nose of the living body, the calculator is configured to:
   calculate a change in a blood flow with time and a change in a blood oxygen saturation level with time in the cheek and a change in a blood flow with time and a change in a blood oxygen saturation level with time in the nose using the first and second image signals, and
   based on comparison between the change in the blood flow with time and the change in the blood oxygen saturation level with time in the cheek and the change in the blood flow with time and the change in the blood oxygen saturation level with time in the nose, generate information representing at least one selected from the group consisting of physical condition, emotion, and concentration of the living body.

12. The biological information detection apparatus according to claim 1, wherein the imaging system further includes:
   an image sensor including an imaging surface in which the first photodetector cells are arrayed;
   an optical system forming the first image on the imaging surface; and
   an adjustment mechanism adjusting a focal point of the optical system, wherein
   the adjustment mechanism adjusts the focal point so as to maximize contrast of the first image.

13. The biological information detection apparatus according to claim 1, wherein the imaging system generates the second image signal based on the environmental light other than light from the light source detected by the second photodetector cells.

14. The biological information detection apparatus according to claim 1, wherein
   the calculator is configured to:
   estimate an influence of surface reflected light based on the first image signal, and calculate the biological information based on the estimated influence of the surface reflected light and the second image signal.

15. The biological information detection apparatus according to claim 1, wherein
   when the brightness of the environmental light is within the high level, the calculator is configured to:
   turn off the light source,
   select the second image signal, and
   calculate the biological information based the second image signal.

16. The biological information detection apparatus according to claim 1, wherein:
   the imaging system includes linear polarization filter,
   the first photodetector cells detect light in the near-infrared wavelength range passing through the linear polarization filter, and
   the second photodetector cells detect light in the visible wavelength range not passing through the linear polarization filter.

17. The biological information detection apparatus according to claim 1, wherein the light source includes a near-infrared laser.

* * * * *